United States Patent
Scholl et al.

(10) Patent No.: US 10,988,801 B2
(45) Date of Patent: Apr. 27, 2021

(54) ENUMERATION OF NUCLEIC ACIDS

(71) Applicant: Esoterix Genetic Laboratories, LLC, Burlington, NC (US)

(72) Inventors: Thomas Scholl, Westborough, MA (US); Brant Hendrickson, Shrewsbury, MA (US)

(73) Assignee: Esoterix Genetic Laboratories, LLC, Burlington, NC (US)

( * ) Notice: Subject to any disclaimer, the term of this patent is extended or adjusted under 35 U.S.C. 154(b) by 0 days.

(21) Appl. No.: 16/210,426

(22) Filed: Dec. 5, 2018

(65) Prior Publication Data

US 2019/0292585 A1 Sep. 26, 2019

Related U.S. Application Data

(63) Continuation of application No. 13/155,008, filed on Jun. 11, 2011, now abandoned.

(60) Provisional application No. 61/352,062, filed on Jun. 7, 2010.

(51) Int. Cl.
*C12Q 1/6851* (2018.01)

(52) U.S. Cl.
CPC ............................... *C12Q 1/6851* (2013.01)

(58) Field of Classification Search
CPC ............ C12Q 1/6851; C12Q 2531/113; C12Q 2545/113; C12Q 2565/518
See application file for complete search history.

(56) References Cited

U.S. PATENT DOCUMENTS

| | | | |
|---|---|---|---|
| 7,439,346 | B2 | 10/2008 | Johnson et al. |
| 8,430,346 | B2 | 4/2013 | Michael |
| 2003/0096239 | A1 | 5/2003 | Gunderson et al. |
| 2012/0015842 | A1 | 1/2012 | Scholl et al. |
| 2014/0227691 | A1 | 8/2014 | May et al. |

FOREIGN PATENT DOCUMENTS

| | | |
|---|---|---|
| CN | 1950519 | 4/2007 |
| CN | 103069005 | 4/2013 |
| JP | 2006511239 | 4/2006 |
| JP | 2013528061 | 7/2013 |
| WO | 2004083443 | 9/2004 |
| WO | 2008014485 | 1/2008 |
| WO | 2008070352 | 6/2008 |
| WO | 2011156387 | 10/2012 |

OTHER PUBLICATIONS

U.S. Appl. No. 13/155,008, "Final Office Action", dated Dec. 18, 2013, 12 Pages.
U.S. Appl. No. 13/155,008, "Final Office Action", dated Jul. 6, 2018, 19 pages.
U.S. Appl. No. 13/155,008, "Final Office Action", dated Oct. 24, 2016, 19 pages.
U.S. Appl. No. 13/155,008, "Non-Final Office Action", dated Apr. 6, 2017, 13 pages.
U.S. Appl. No. 13/155,008, "Non-Final Office Action", dated Feb. 19, 2016, 13 pages.
U.S. Appl. No. 13/155,008, "Non-Final Office Action", dated Nov. 24, 2017, 16 pages.
Butz et al., "Detecting Changes in the Relative Expression of KRAS2 Splice Variants Using Polymerase Colonies", Biotechnology Progress, vol. 20, No. 6, Dec. 2004, pp. 1836-1839.
Butz et al., "Detection of Allelic Variations of Human Gene Expression by Polymerase Colonies", BMC Genetics, vol. 5, Feb. 2004, pp. 3-8.
Chu et al., "A microarray-based approach for the identification of epigenetic biomarkers for the noninvasive diagnosis of fetal disease", Prenatal Diagnosis, vol. 29, Nov. 29, 2009, pp. 1020-1030.
CN201180030604.5, "Office Action", dated Nov. 4, 2014, 20 pages.
CN201180030604.5, "Office Action", dated Feb. 12, 2014, 21 pages.
Fedurco et al., "BTA, a novel reagent for DNA attachment on glass and efficient generation of solid-phase amplified DNA colonies", Nucleic Acids Research vol. 34, No. 3, 2006, p. e22.
JP2013-514306, "Office Action", dated Jun. 23, 2015, 8 pages.
Kim et al., "Polony Multiplex Analysis of Gene Expression (PMAGE) in Mouse Hypertrophic Cardiomyopathy", Science, vol. 316, No. 5830, Jun. 8, 2007, 1481-1484.
Milan et al., "BTA, a novel reagent for DNA attachment on glass and efficient generation of solid-phase amplified DNA colonies", Nucleic Acids Research, vol. 34, No. 3, 2006, 1-13.
Nardi et al., "Ouantitative monitoring by polymerase colony assay of known mutations resistant to ABL kinase inhibitors", Oncogene, vol. 27, No. 6, Jan. 31, 2008, pp. 775-782.
PCT/US11/39460, "International Search Report and Written Opinion", dated Aug. 9, 2012, 14.
Rieger et al., "Polony analysis of gene expression in ES cells and blastocysts", Nucleic Acids Research 2007 LNKD-PUBMED: 18073198, vol. 35, No. 22, 2007, p. e151.
SG201208623-7, "Office Action", dated Jun. 27, 2014, 7 pages.
Voelkerding et al., "Next-Generation Sequencing: from Basic Research to Diagnostics", Clinical Chemistry, vol. 55, Issue 4, Feb. 2009, pp. 641-658.

(Continued)

*Primary Examiner* — Cynthia B Wilder
(74) *Attorney, Agent, or Firm* — Kilpatrick Townsend & Stockton LLP

(57) ABSTRACT

Disclosed are methods and systems for enumeration of nucleic acids, including for the detection of rare events in a biological sample. In certain embodiments, the method may comprise arranging polynucleotides obtained from a biological sample to form a plurality of reaction sites, wherein each reaction site contains on average one polynucleotide; amplifying the polynucleotides in the plurality of reaction sites; determining by nucleic acid hybridization (i) a first number of first reaction sites containing a target nucleic acid sequence, or a portion thereof, and (ii) a second number of second reaction sites containing a reference nucleic acid sequence, or a portion thereof; comparing the first number of the first reaction sites to the second number of the second reaction sites to determine the relative amount of the target nucleic acid in the biological sample.

15 Claims, No Drawings
Specification includes a Sequence Listing.

(56) References Cited

OTHER PUBLICATIONS

Zhang et al., "Single-Molecule DNA Amplification and Analysis Using Microfluidics", Chemical reviews, vol. 110, No. 8, Apr. 2010, pp. 4910-4947.

Zhang et al., "Long-Range Polony Haplotyping of Individual Human Chromosome Molecules", Nature Genetics, vol. 38, No. 3, Mar. 2006, pp. 382-387.

ENUMERATION OF NUCLEIC ACIDS

RELATED APPLICATIONS

This application is a continuation of U.S. patent application Ser. No. 13/155,008 filed Jun. 7, 2011, which claims priority to U.S. Provisional Application No. 61/352,062 filed Jun. 7, 2010. These applications are each incorporated herein by reference in their entireties.

REFERENCE TO SUBMISSION OF A SEQUENCE LISTING AS A TEXT FILE

The Sequence Listing written in file SequenceListing-111778.txt, 808 bytes, machine format IBM-PC, MS-Windows operating system, is hereby incorporated by reference in its entirety.

FIELD OF THE INVENTION

The present invention relates to methods and systems for enumeration of nucleic acids that may be used to detect rare events, such as fetal aneuploidies, cancer detection and infectious diseases.

BACKGROUND

Early detection of mutations and determination of imbalance of nucleic acids present in diseased cells can have important clinical implications. For example, cancer cells may carry mutations that are not present in normal cells and detection of such mutations may help early diagnosis of cancer. An individual having less than two normal copies of an autosomal gene may be at increased risk of developing a disease and/or be a carrier for the disease. As another example, aneuploidy is defined as an abnormal number of whole chromosomes or parts of chromosomes causing a genetic imbalance which may be lethal at early stages of development, cause miscarriage in later pregnancy or result in a viable but abnormal pregnancy. The most frequent and clinically significant aneuploidies involve single chromosomes (strictly "aneusomy") in which there are either three ("trisomy") or only one ("monosomy") instead of the normal pair of chromosomes. Thus, accurate enumeration of nucleic acids such as chromosomes can have life-changing consequences. Therefore, there is a great need for more accurate and sensitive methods for detecting mutations and/or genomic imbalance.

SUMMARY OF THE INVENTION

The present invention provides more accurate, efficient and sensitive methods and systems for analyzing (e.g., detecting and/or enumerating) target nucleic acids in biological samples. Among other things, the present invention provides methods and systems for precise enumeration of nucleic acid molecules based on single molecule amplification and hybridization-based probing. In addition, the invention is useful for detecting rare events including mutations associated with diseases and conditions.

In one aspect, the present invention provides a method of determining the relative amount of a target nucleic acid in a biological sample. In some embodiments, inventive methods according to the present invention include steps of arranging polynucleotides obtained from a biological sample to form a plurality of reaction sites, wherein each reaction site contains on average one polynucleotide; amplifying the polynucleotides in the plurality of reaction sites; determining by nucleic acid hybridization (i) a first number of first reaction sites containing a target nucleic acid sequence, or a portion thereof, and (ii) a second number of second reaction sites containing a reference nucleic acid sequence, or a portion thereof; and comparing the first number of the first reaction sites to the second number of the second reaction sites to determine the relative amount of the target nucleic acid in the biological sample.

In contrast to other methods that have previously been described, such as massively parallel sequencing, the present invention provides a faster, more efficient and less costly method for determining the relative amount of a target nucleic acid in a biological sample. In some embodiments, inventive methods according to the present invention include providing 5 million copies of genomic information arranged in PCR clones (polonies) on a PCR substrate; millions of PCR probes for desired sequences, each labeled with a different detectable label may then be hybridized to the substrate; excess label is removed and the number and identity of each detectable label may be determined by known methods; relative amounts of target nucleic acids may be determined by normalizing ratios of target sequences against known reference sequences as has previously been described.

In another aspect, embodiments of the present invention may be used as an additional prenatal screening tool for patients who have positive results from a serum screen or for patients who are considered "high risk." Embodiments of the present invention, as described in detail herein, may be utilized during the first trimester as early as 4-6 weeks gestation. In other embodiments, the methods of the present invention may be utilized after a positive serum screen at approximately 12 weeks gestation. Embodiments of the present invention may exhibit 100% sensitivity with less than 1% false positives.

In some embodiments, inventive methods according to the present invention include steps of arranging polynucleotides obtained from a biological sample to form a plurality of amplification sites, wherein each amplification site contains on average one polynucleotide; amplifying polynucleotides in the plurality of amplification sites to generate amplified products; hybridizing the amplified products with nucleic acid probes specific for (i) a target nucleic acid, or a portion thereof, and (ii) a reference nucleic acid, or a portion thereof, in a plurality of detection sites, wherein each detection site contains on average one polynucleotide from the amplified products; determining (i) a first number of first detection sites containing probes hybridized to a target nucleic acid, or a portion thereof, and (ii) a second number of second detection sites containing probes hybridized to a reference nucleic acid, or a portion thereof; and comparing the first number of the first detection sites to the second number of the second detection sites to determine the relative amount of the target nucleic acid in the biological sample. In some embodiments, inventive methods according to the invention further include a step of harvesting the amplified products before the hybridizing step. In some embodiments, the hybridizing step is carried out with a microarray.

In some embodiments, the arranging step is performed using a solid, semi-solid and/or liquid support. In some embodiments, the arranging step is performed on a solid support. In some embodiments, suitable solid support is selected from the group consisting of glasses, optical fiber, silica, microchips, plastics, beads; biofilms, cellulose.

In some embodiments, the arranging step comprises a step of using flowcell technology. In some embodiments, the arranging step comprises a step of distributing the collection of nucleic acid molecules within a gel matrix. In some embodiments, the arranging step comprises a step of mixing the collection of nucleic acid molecules with emulsion beads.

In some embodiments, the support comprises a plurality of capturing moieties immobilized thereon to capture individual polynucleotide. In some embodiments, the capturing moieties comprise capturing oligonucleotides.

In some embodiments, inventive methods of the present invention further include a step of first treating the polynucleotides such that individual polynucleotides contain adapter sequences at the 5' and 3' ends, wherein the adapter sequences hybridize to the capturing oligonucleotides immobilized on the support.

In some embodiments, the amplifying step comprises performing a PCR reaction. In some embodiments, the amplifying step comprises performing rolling circle amplification.

In some embodiments, the target nucleic acid to be enumerated is a target chromosome. In some embodiments, the target chromosome is selected from chromosome X, Y, 13, 18, or 21. In other embodiments, the target chromosome may comprise chromosome 4, 5, 8, 9, 11, 15, 16, 17 or 22. In some embodiments, the reference nucleic acid is a reference chromosome. In some embodiments, the reference chromosome is chromosome 1, 2, 6, 11, X, Y, 13, 18, or 21. In other embodiments, the reference chromosome may comprise chromosome 4, 5, 8, 9, 11, 15, 16, 17 or 22.

In some embodiments, the target nucleic acid contains a mutation. In some embodiments, the mutation is selected from the group consisting of single nucleotide polymorphisms (SNPs), deletions, insertions, duplications, and combinations thereof.

In some embodiments, the biological sample to be analyzed contains over-abundance or under-abundance of the target nucleic acid. In some embodiments, the biological sample contains aneuploid chromosomes.

In some embodiments, suitable nucleic acid probes specific for the target nucleic acid, or a portion thereof, are specific for a single locus. In some embodiments, suitable nucleic acid probes specific for the target nucleic acid, or a portion thereof, are specific for multiple loci. In some embodiments, suitable nucleic acid probes specific for the target nucleic acid, or a portion thereof, are multiplexed. In alternate embodiments, suitable multiplexed probes comprise anywhere from 2-10,000 probes. In some embodiments, suitable multiplexed probes comprise about 200, or 300, or 400, or 500, or 600, or 700, or 800, or 900, or 1,000, or 1,500, or 2,000, or 2,500, or 3,000, or 3,500, or 4,000, or 5,000, or 6,000, or 7,000, or 8,000, or 9,000 probes. In some embodiments, suitable multiplexed probes comprise about 500 probes.

In some embodiments, suitable nucleic acid probes specific for the reference nucleic acid, or a portion thereof, are specific for a single locus. In some embodiments, suitable nucleic acid probes specific for the target nucleic acid, or a portion thereof, are specific for multiple loci. In some embodiments, suitable nucleic acid probes specific for the reference nucleic acid, or a portion thereof, are multiplexed. In alternate embodiments, suitable multiplexed probes comprise anywhere from 2-10,000 probes. In some embodiments, suitable multiplexed probes comprise about 200, or 300, or 400, or 500, or 600, or 700, or 800, or 900, or 1,000, or 1,500, or 2,000, or 2,500, or 3,000, or 3,500, or 4,000, or 5,000, or 6,000, or 7,000, or 8,000, or 9,000 probes. In some embodiments, suitable multiplexed probes comprise about 500 probes.

In some embodiments, the probes specific for the target nucleic acid, or a portion thereof, and the probes specific for the reference nucleic acid, or a portion thereof, are labeled with distinctively detectable signals. In some embodiments, the distinctively detectable signals are different optical signals. In some embodiments, the different optical signals are distinct fluorescent or luminescent signals.

In some embodiments, the determining step comprises determining the relative copy number of the target nucleic acid. In some embodiments, the step of determining the relative copy number of the target nucleic acid comprises the steps of (a) determining a first fluorescent signal level indicative of the first number of the detection sites containing the target nucleic acid, or a portion thereof, normalized to the background signals; (b) determining a second fluorescent signal level indicative of the second number of the detection sites containing the reference nucleic acid, or a portion thereof, normalized to the background signals; (c) determining a ratio of the first fluorescent signal level to the second fluorescent signal level; and (d) determining the relative copy number of the target nucleic acid by normalizing the ratio determined at step (c) to the ratio between the number of probes specific for the target nucleic acid and the number of probes specific for the reference nucleic acid.

In some embodiments, the polynucleotides obtained from the biological sample contain genomic DNA in an amount less than one genome equivalence. In some embodiments, the amplified products contain amplified genomic DNA at a pre-determined level of genome equivalence.

In some embodiments, less than 1% of the polynucleotides obtained from the biological sample represent the target nucleic acid. In some embodiments, less than 0.1% of the polynucleotides obtained from the biological sample represent the target nucleic acid. In some embodiments, less than 1 out of a million of the polynucleotides obtained from the biological sample represent the target nucleic acid. In some embodiments, less than 1 out of 10 million of the polynucleotides obtained from the biological sample represent the target nucleic acid. Or, the polynucleotides obtained from the biological sample may fall within these ranges.

In some embodiments, the target nucleic acid is derived from a fetal cell. In some embodiments, the target nucleic acid comprises a fetal chromosome. In some embodiments, the target nucleic acid is derived from a diseased cell (e.g., a cancer cell) or a plurality of cancer cells that may be of the same origin or may have different origins (e.g., a primary cancer and a metastasis).

In some embodiments, inventive methods according to the present invention further include a step of whole genome amplification prior to the arranging step.

In some embodiments, inventive methods of the present invention further include a step of determining if the relative amount of the target nucleic acid is abnormal as compared to a control. In some embodiments, inventive methods of the present invention are used to detect a disease, disorder or condition, or a carrier thereof, associated with the abnormal amount of the target nucleic acid. In some embodiments, inventive methods of the present invention are used for prenatal diagnosis of fetal aneuploidy.

In some embodiments, a suitable biological sample is selected from the group consisting of cells, tissue, whole blood, plasma, serum, urine, stool, saliva, cord blood, chorionic villus sample, chorionic villus sample culture, amniotic fluid, amniotic fluid culture, transcervical lavage fluid, and combination thereof. Or other biological samples (e.g., tissue biopsies) may be used.

In another aspect, the present invention also provides systems for performing various methods described herein. In some embodiments, the present invention provides a system for determining the relative amount of a target nucleic acid, comprising a component to amplify polynucleotides on a plurality of amplification sites to generate amplified products; a component to carry out hybridization of the amplified products with probes labeled with first detectable signals that are specific for a target nucleic acid, or a portion thereof, and probes labeled with second detectable signals that are specific for a reference nucleic acid, or a portion thereof; a component (e.g., a determination module) adapted to determine the level of the first detectable signals, and determine the level of the second detectable signals; a component (e.g., a storage device) configured to store signal information from the determination module and the information provided by a user indicative of the number of the probes specific for the target nucleic acid, or a portion thereof, and the number of the probes specific for the reference nucleic acid, or a portion thereof; and a component (e.g., a computing module) adapted to calculate the ratio of the level of the first detectable signals to the level of the second detectable signals and determine the relative amount of the target nucleic acid by normalizing the ratio of the signal levels to the ratio between the number of the probes specific for the target nucleic acid, or a portion thereof, and the number of the probes specific for the reference nucleic acid, or a portion thereof.

In yet another aspect, the present invention provides methods and systems for detecting rare events in a biological sample. In some embodiments, the present invention provides a method of detecting a target nucleic acid in a biological sample, comprising arranging polynucleotides obtained from the biological sample to form a plurality of reaction sites, wherein each reaction site contains on average one polynucleotide; amplifying the polynucleotides in the plurality of reaction sites to generate a plurality of clusters such that each cluster contains amplified nucleic acid product; and detecting clusters or reaction sites containing the target nucleic acid, or a portion thereof, by hybridization using one or more probes specific for the target nucleic acid, thereby detecting the target nucleic acid in the biological sample. Each of the alternate embodiments described herein refers to any of the methods or systems of the invention unless stated otherwise.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Other features, objects, and advantages of the present invention are apparent in the detailed description and claims that follow. It should be understood, however, that the detailed description, and the claims, while indicating embodiments of the present invention, are given by way of illustration only, not limitation. Various changes and modifications within the scope of the invention will become apparent to those skilled in the art.

DEFINITIONS

In order for the present invention to be more readily understood, certain terms are first defined below. Additional definitions for the following terms and other terms are set forth throughout the specification.

Allele: As used herein, the phrase "allele" is used interchangeably with "allelic variant" and refers to a variant of a locus or gene. In some embodiments, a particular allele of a locus or gene is associated with a particular phenotype, for example, altered risk of developing a disease or condition, likelihood of progressing to a particular disease or condition stage, amenability to particular therapeutics, susceptibility to infection, immune function, etc.

Amplification: As used herein, the term "amplification" refers to any methods known in the art for copying a target nucleic acid, thereby increasing the number of copies of a selected nucleic acid sequence. Amplification may be exponential or linear. A target nucleic acid may be either DNA or RNA. Typically, the sequences amplified in this manner form an "amplicon." Amplification may be accomplished with various methods including, but not limited to, the polymerase chain reaction ("PCR"), transcription-based amplification, isothermal amplification, rolling circle amplification, etc. Amplification may be performed with relatively similar amount of each primer of a primer pair to generate a double stranded amplicon. However, asymmetric PCR may be used to amplify predominantly or exclusively a single stranded product as is well known in the art (e.g., Poddar et al. *Molec. And Cell. Probes* 14:25-32 (2000)). This can be achieved using each pair of primers by reducing the concentration of one primer significantly relative to the other primer of the pair (e.g., 100 fold difference). Amplification by asymmetric PCR is generally linear. A skilled artisan will understand that different amplification methods may be used together.

Aneuploidy: As used herein, the term "aneuploidy" refers to an abnormal number of whole chromosomes or parts of chromosomes. Typically, aneuploidy causes a genetic imbalance which may be lethal at early stages of development, cause miscarriage in later pregnancy or result in a viable but abnormal pregnancy. The most frequent and clinically significant aneuploidies involve single chromosomes (strictly "aneusomy") in which there are either three ("trisomy") or only one ("monosomy") instead of the normal pair of chromosomes.

Animal: As used herein, the term "animal" refers to any member of the animal kingdom. In some embodiments, "animal" refers to humans, at any stage of development including humans that have not yet been born (e.g., a fetus). In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biological sample: As used herein, the term "biological sample" encompasses any sample obtained from a biological source. A biological sample can, by way of non-limiting example, include blood, amniotic fluid, sera, urine, feces, epidermal sample, skin sample, cheek swab, sperm, amniotic fluid, cultured cells, bone marrow sample, tissue biopsy and/or chorionic villi. Convenient biological samples may be obtained by, for example, scraping cells from the surface of the buccal cavity. Cell cultures of any biological samples can also be used as biological samples, e.g., cultures of chorionic villus samples and/or aminoitic fluid cultures such as amniocyte cultures. A biological sample can also be, e.g., a sample obtained from any organ or tissue (including a biopsy or autopsy specimen), can comprise cells (whether primary cells or cultured cells), medium conditioned by any cell, tissue or organ, tissue culture. In some embodiments, biological samples suitable for the invention are samples which have been processed to release or otherwise make available a nucleic acid for detection as described herein. Suitable biological samples may be obtained from a stage of life such as a fetus, young adult, adult (e.g., pregnant women), and the like. Fixed or frozen tissues also may be used. The terms "biological sample" and "biological specimen" are used interchangeably.

Carrier: As used herein, the phrase "carrier" refers to an individual that harbors a genetic mutation or allelic variant but displaying no symptoms of a disease associated with the genetic mutation or allelic variant. A carrier, however, is typically able to pass the genetic mutation or allelic variant onto their offspring, who may then express the mutated gene or allelic variant. Typically, this phenomenon is a result of the recessive nature of many genes. In certain embodiments, the mutation or allelic variant that the carrier harbors predisposes or is associated with a particular phenotype, for example, altered risk of developing a disease or condition, likelihood of progressing to a particular disease or condition stage, amenability to particular therapeutics, susceptibility to infection, immune function, etc. Without limitation, a carrier may have reduced or increased copy numbers of a gene or a portion of a gene. A carrier may also harbor mutations (e.g., point mutations, polymorphisms, deletions, insertions or translocations, etc.) within a gene. A "carrier" is also referred to as a "genetic carrier" herein.

Copy number: As used herein, the phrase "copy number" when used in reference to a locus, refers to the number of copies of such a locus present per genome or genome equivalent. A "normal copy number" when used in reference to a locus, refers to the copy number of a normal or wild-type allele present in a normal individual. In certain embodiments, the copy number ranges from zero to two, inclusive. In certain embodiments, the copy number ranges from zero to three, zero to four, zero to six, zero to seven, or zero to more than seven copies, inclusive. In embodiments in which the copy number of a locus varies greatly across individuals in a population, an estimated median copy number could be taken as the "normal copy number" for calculation and/or comparison purposes.

Coding sequence vs. non-coding sequence: As used herein, the term "coding sequence" refers to a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom. As used herein, the term "non-coding sequence" refers to a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

Complement: As used herein, the terms "complement," "complementary" and "complementarity" refer to the pairing of nucleotide sequences according to Watson/Crick pairing rules. For example, a sequence 5'-GCGGTCCCA-3' (SEQ ID NO: 1) has the complementary sequence of 5'-TGGGACCGC-3' (SEQ ID NO: 2). A complement sequence can also be a sequence of RNA complementary to the DNA sequence. Certain bases not commonly found in natural nucleic acids may be included in the complementary nucleic acids including, but not limited to, inosine, 7-deazaguanine, Locked Nucleic Acids (LNA), and Peptide Nucleic Acids (PNA). Complementarity need not be perfect; stable duplexes may contain mismatched base pairs, degenerative, or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Control: As used herein, the term "control" has its art-understood meaning of being a standard against which results are compared. Typically, controls are used to augment integrity in experiments by isolating variables in order to make a conclusion about such variables. In some embodiments, a control is a reaction or assay that is performed simultaneously with a test reaction or assay to provide a comparator. In one experiment, the "test" (i.e., the variable being tested) is applied. In the second experiment, the "control," the variable being tested is not applied. In some embodiments, a control is a historical control (i.e., of a test or assay performed previously, or an amount or result that is previously known). In some embodiments, a control is or comprises a printed or otherwise saved record. A control may be a positive control or a negative control.

Crude: As used herein, the term "crude," when used in connection with a biological sample, refers to a sample that is in a substantially unrefined state. For example, a crude sample can be cell lysates or biopsy tissue sample. A crude sample may exist in solution or as a dry preparation.

Deletion: As used herein, the term "deletion" encompasses a mutation that removes one or more nucleotides from a naturally-occurring nucleic acid.

Flanking: As used herein, the term "flanking" is meant that a primer hybridizes to a target nucleic acid adjoining a region of interest sought to be amplified on the target. The skilled artisan will understand that preferred primers are pairs of primers that hybridize 3' from a region of interest, one on each strand of a target double stranded DNA molecule, such that nucleotides may be add to the 3' end of the primer by a suitable DNA polymerase.

Gene: As used herein, the term "gene" refers to a discrete nucleic acid sequence responsible for a discrete cellular (e.g., intracellular or extracellular) product and/or function. More specifically, the term "gene" refers to a nucleic acid that includes a portion encoding a protein and optionally encompasses regulatory sequences, such as promoters, enhancers, terminators, and the like, which are involved in the regulation of expression of the protein encoded by the gene of interest. As used herein, the term "gene" can also include nucleic acids that do not encode proteins but rather provide templates for transcription of functional RNA molecules such as tRNAs, rRNAs, etc. Alternatively, a gene may define a genomic location for a particular event/function, such as a protein and/or nucleic acid binding site.

Genotype: As used herein, the term "genotype" refers to the genetic constitution of an organism. More specifically, the term refers to the identity of alleles present in an individual. "Genotyping" of an individual or a DNA sample refers to identifying the nature, in terms of nucleotide base, of the two alleles possessed by an individual at a known polymorphic site.

Heterozygous: As used herein, the term "heterozygous" or "HET" refers to an individual possessing two different alleles of the same gene. As used herein, the term "heterozygous" encompasses "compound heterozygous" or "compound heterozygous mutant." As used herein, the term "compound heterozygous" refers to an individual possessing two different alleles. As used herein, the term "compound heterozygous mutant" refers to an individual possessing two different copies of an allele, such alleles are characterized as mutant forms of a gene. The term "mutant" as used herein refers to a mutated, or potentially non-functional form of a gene.

Homozygous: As used herein, the term "homozygous" refers to an individual possessing two copies of the same allele. As used herein, the term "homozygous mutant" refers to an individual possessing two copies of the same allele, such allele being characterized as the mutant form of a gene. The term "mutant" as used herein refers to a mutated, or potentially non-functional form of a gene.

Hybridize: As used herein, the term "hybridize" or "hybridization" refers to a process where two complementary nucleic acid strands anneal to each other under appropriately stringent conditions. Oligonucleotides or probes suitable for hybridizations typically contain 10-100 nucleotides in length (e.g., 18-50, 12-70, 10-30, 10-24, 18-36 nucleotides in length). Nucleic acid hybridization techniques are well known in the art. See, e.g., Sambrook, et al, 1989, Molecular Cloning: A Laboratory Manual, Second Edition, Cold Spring Harbor Press, Plainview, N.Y. Those skilled in the art understand how to estimate and adjust the stringency of hybridization conditions such that sequences having at least a desired level of complementarity will stably hybridize, while those having lower complementarity will not. For examples of hybridization conditions and parameters, see, e.g., Sambrook, et al., 1989, Molecular Cloning: A Laboratory Manual, Second Edition, Cold Spring Harbor Press, Plainview, N.Y.; Ausubel, F. M. et al. 1994, Current Protocols in Molecular Biology, John Wiley & Sons, Secaucus, N.J.

Individually resolved: As used herein, the term "individually resolved" is used herein to indicate that, when visualized, it is possible to distinguish one polymer or clone from its neighboring polymers or clones. Visualization may be effected by the use of reporter labels, e.g. fluorophores, the signal of which is individually resolved. The requirement for individual resolution ensures that individual monomer incorporation can be detected at each synthesis step.

Insertion or addition: As used herein, the term "insertion" or "addition" refers to a change in an amino acid or nucleotide sequence resulting in the addition of one or more amino acid residues or nucleotides, respectively, as compared to the naturally occurring molecule.

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism such as a non-human animal.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Labeled: The terms "labeled" and "labeled with a detectable agent or moiety" are used herein interchangeably to specify that an entity (e.g., a nucleic acid probe, antibody, etc.) can be visualized, for example following binding to another entity (e.g., a nucleic acid, polypeptide, etc.). The detectable agent or moiety may be selected such that it generates a signal which can be measured and whose intensity is related to (e.g., proportional to) the amount of bound entity. A wide variety of systems for labeling and/or detecting proteins and peptides are known in the art. Labeled proteins and peptides can be prepared by incorporation of, or conjugation to, a label that is detectable by spectroscopic, photochemical, biochemical, immunochemical, electrical, optical, chemical or other means. A label or labeling moiety may be directly detectable (i.e., it does not require any further reaction or manipulation to be detectable, e.g., a fluorophore is directly detectable) or it may be indirectly detectable (i.e., it is made detectable through reaction or binding with another entity that is detectable, e.g., a hapten is detectable by immunostaining after reaction with an appropriate antibody comprising a reporter such as a fluorophore). Suitable detectable agents include, but are not limited to, radionucleotides, fluorophores, chemiluminescent agents, microparticles, enzymes, colorimetric labels, magnetic labels, haptens, molecular beacons, aptamer beacons, and the like.

Locus: As used herein, the term "locus" refers the specific location of a particular DNA sequence on a chromosome. As used herein, a particular DNA sequence can be of any length (e.g., one, two, three, ten, fifty, or more nucleotides). In some embodiments, the locus is or comprises a gene or a portion of a gene. In some embodiments, the locus is or comprises an exon or a portion of an exon of a gene. In some embodiments, the locus is or comprises an intron or a portion of an intron of a gene. In some embodiments, the locus is or comprises a regulatory element or a portion of a regulatory element of a gene. In some embodiments, the locus is associated with a disease, disorder, and/or condition. For example, mutations at the locus (including deletions, insertions, splicing mutations, point mutations, etc.) may be correlated with a disease, disorder, and/or condition.

Karyotyping: As used herein, the term "karyotyping" encompasses a determination of the number of chromosomes in a eukaryote cell.

Normal: As used herein, the term "normal," when used to modify the term "copy number" or "locus" or "gene" or "allele," refers to the copy number or locus, gene, or allele that is present in the highest percentage in a population, e.g., the wild-type number or allele. When used to modify the term "individual" or "subject" they refer to an individual or group of individuals who carry the copy number or the locus, gene or allele that is present in the highest percentage in a population, e.g., a wild-type individual or subject. Typically, a normal "individual" or "subject" does not have a particular disease or condition and is also not a carrier of the disease or condition. The term "normal" is also used herein to qualify a biological specimen or sample isolated from a normal or wild-type individual or subject, for example, a "normal biological sample."

Multiplex PCR: As used herein, the term "multiplex PCR" refers to amplification of two or more regions which are each primed using a distinct primers pair.

Primer: As used herein, the term "primer" refers to a short single-stranded oligonucleotide capable of hybridizing to a complementary sequence in a nucleic acid sample. Typically, a primer serves as an initiation point for template dependent DNA synthesis. Deoxyribonucleotides can be added to a primer by a DNA polymerase. In some embodiments, such deoxyribonucleotides addition to a primer is also known as primer extension. The term primer, as used herein, includes all forms of primers that may be synthesized including peptide nucleic acid primers, locked nucleic acid primers, phosphorothioate modified primers, labeled primers, and the like. A "primer pair" or "primer set" for a PCR reaction typically refers to a set of primers typically including a "forward primer" and a "reverse primer." As used herein, a "forward primer" refers to a primer that anneals to the anti-sense strand of dsDNA. A "reverse primer" anneals to the sense-strand of dsDNA.

Polymorphism: As used herein, the term "polymorphism" refers to the coexistence of more than one form of a gene or portion thereof.

Probe: As used herein, the term "probe," when used in reference to a probe for a nucleic acid, refers to a nucleic acid molecule having specific nucleotide sequences (e.g., RNA or DNA) that can bind or hybridize to nucleic acids of interest. Typically, probes specifically bind (or specifically hybridize) to nucleic acid of complementary or substantially complementary sequence through one or more types of chemical bonds, usually through hydrogen bond formation. In some embodiments, probes can bind to nucleic acids of DNA amplicons in a real-time PCR reaction.

Sense strand vs. anti-sense strand: As used herein, the term "sense strand" refers to the strand of double-stranded DNA (dsDNA) that includes at least a portion of a coding sequence of a functional protein. As used herein, the term "anti-sense strand" refers to the strand of dsDNA that is the reverse complement of the sense strand.

Signal: As used herein, the term "signal" refers to a detectable and/or measurable entity. In certain embodiments, the signal is detectable by the human eye, e.g., visible. For example, the signal could be or could relate to intensity and/or wavelength of color in the visible spectrum. Non-limiting examples of such signals include colored precipitates and colored soluble products resulting from a chemical reaction such as an enzymatic reaction. In certain embodiments, the signal is detectable using an apparatus. In some embodiments, the signal is generated from a fluorophore that emits fluorescent light when excited, where the light is detectable with a fluorescence detector. In some embodiments, the signal is or relates to light (e.g., visible light and/or ultraviolet light) that is detectable by a spectrophotometer. For example, light generated by a chemiluminescent reaction could be used as a signal. In some embodiments, the signal is or relates to radiation, e.g., radiation emitted by radioisotopes, infrared radiation, etc. In certain embodiments, the signal is a direct or indirect indicator of a property of a physical entity. For example, a signal could be used as an indicator of amount and/or concentration of a nucleic acid in a biological sample and/or in a reaction vessel.

Specific: As used herein, the term "specific," when used in connection with an oligonucleotide primer, refers to an oligonucleotide or primer, under appropriate hybridization or washing conditions, is capable of hybridizing to the target of interest and not substantially hybridizing to nucleic acids which are not of interest. Higher levels of sequence identity are preferred and include at least 60%, 65%, 70%, 75%, 80%, 85%, 90%, 91%, 92%, 93%, 94%, 95%, 96%, 97%, 98%, 99%, or 100% sequence identity. In some embodiments, a specific oligonucleotide or primer contains at least 4, 6, 8, 10, 12, 14, 16, 18, 20, 22, 24, 26, 28, 30, 35, 40, 45, 50, 55, 60, 65, 70, or more bases of sequence identity with a portion of the nucleic acid to be hybridized or amplified when the oligonucleotide and the nucleic acid are aligned.

Subject: As used herein, the term "subject" refers to a human or any non-human animal (e.g., mouse, rat, rabbit, dog, cat, cattle, swine, sheep, horse or primate). A human includes pre-natal and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially complementary: As used herein, the term "substantially complementary" refers to two sequences that can hybridize under stringent hybridization conditions. The skilled artisan will understand that substantially complementary sequences need not hybridize along their entire length. In some embodiments, "stringent hybridization conditions" refer to hybridization conditions at least as stringent as the following: hybridization in 50% formamide, 5×SSC, 50 mM $NaH_2PO_4$, pH 6.8, 0.5% SDS, 0.1 mg/mL sonicated salmon sperm DNA, and 5× Denhart's solution at 42° C. overnight; washing with 2×SSC, 0.1% SDS at 45° C.; and washing with 0.2×SSC, 0.1% SDS at 45° C. In some embodiments, stringent hybridization conditions should not allow for hybridization of two nucleic acids which differ over a stretch of 20 contiguous nucleotides by more than two bases.

Substitution: As used herein, the term "substitution" refers to the replacement of one or more amino acids or nucleotides by different amino acids or nucleotides, respectively, as compared to the naturally occurring molecule.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Wild-type: As used herein, the term "wild-type" refers to the typical or the most common form existed in nature.

DETAILED DESCRIPTION

The present invention provides, among other things, methods and systems for analyzing (e.g., detecting and/or enumerating) target nucleic acids in biological samples. In general, the present invention involves single molecule amplification and detection of the amplified products containing target nucleic acids or portions thereof using hybridization-based probing. In some embodiments, suitable probes can be multiplexed to high levels and can be detected through labels such as fluorescent, colorimetric, luminescent, among other means. Thus, the present invention provides sensitive methods of detecting target nucleic acids in a biological sample. The invention is particularly useful in detecting target nucleic acid present as rare events in a biological sample, for example, mutations associated with fetal conditions, diseases such as cancer, infectious diseases, autoimmune diseases, immunological conditions associated with transplant or embryo implant, among others.

In some embodiments, probes can be labeled with different colors attributable to different nucleic acids (e.g., target vs. reference) such that amplified products can be attributed to different nucleic acids (e.g., target vs. reference) and counted. Thus, inventive methods according to the present invention can also be used to determine the relative amount of a target nucleic acid in a biological sample, for example, ratios between target and reference nucleic acids in a biological sample. In some embodiments, probes can be deeply multiplexed and labeled with different colors attributable to different chromosomes such that the amplified products can be attributed to different chromosomes and counted. Differences in the ratios of products attributed to different chromosomes can be used to diagnose aneuploid pregnancy.

Thus, the present invention is especially advantageous because it provides the ability to multiplex locus detection and thereby make especially efficient use of precious specimen beyond that can be achieved by multiplexing TAQMAN probes or other existing approaches known in the art. In many embodiments, the present invention can achieve the same level of efficiency with respect to the use of specimen as high throughput sequencing of single molecule, but achieves these results much more cheaply and rapidly.

Various aspects of the invention are described in detail in the following sections. The use of sections is not meant to limit the invention. Each section can apply to any aspect of the invention. In this application, the use of "or" means "and/or" unless stated otherwise.

Target Nucleic Acids and Associated Genetic Diseases, Disorders and Conditions

The present invention can be used to detect any type of target nucleic acids. In some embodiments, the invention may be used to detect target nucleic acids associated with diseases, disorders or conditions. For example, target nucleic acids may carry mutations such as nucleic acid base substitutions, duplications, insertions, deletions and/or translocations. In some embodiments, the invention may be used to detect mutations associated with rare events in a biological sample. For example, the invention can be used to detect mutations in rare cells present in a biological sample. In some embodiments, such rare cells are cancer cells present in a biological sample (e.g., whole blood) from a patient. In some embodiments, such rare cells are fetal cells present in maternal blood. In some embodiments, such rare cells are pathogens associated with infectious diseases. In some embodiments, such rare cells are immune cells associated with autoimmune diseases or immunological conditions associated with transplant, and the like. Thus, embodiments of the invention can be used for pre-natal diagnosis of fetal abnormalities and early diagnosis of cancer and other pathological conditions.

In some embodiments, the present invention can be used to determine relative amount of a target nucleic acid such as determining ratios between a target and a reference nucleic acid. Therefore, the invention is particularly useful in detecting imbalance of any chromosomes or a number of genetic loci implicated in genetic diseases. Thus, methods disclosed herein can facilitate detection of carriers, diagnosis of patients, prenatal diagnosis, and/or genotyping of embryos for implantation, etc. As appreciated by those of ordinary skill in the art, the genetic disease with which a target nucleic acids is associated can follow any of a number of inheritance patterns, including, for example, autosomal recessive, autosomal dominant, sex-linked dominant, and sex-linked recessive.

In some embodiments, the present invention is particularly adapted to detecting genetic abnormalities that involve quantitative differences between maternal and fetal genetic nucleic acids. These genetic abnormalities include mutations that may be heterozygous and homozygous between maternal and fetal DNA, and aneuploidies. For example, a missing copy of chromosome X (monosomy X) results in Turner's Syndrome, while an additional copy of chromosome 21 results in Down Syndrome. Other diseases such as Edward's Syndrome and Patau Syndrome are caused by an additional copy of chromosome 18, and chromosome 13, respectively. The present method may be used for detection of a translocation, addition, amplification, transversion, inversion, aneuploidy, polyploidy, monosomy, trisomy including but not limited to trisomy 21, trisomy 13, trisomy 14, trisomy 15, trisomy 16, trisomy 18, trisomy 22, triploidy, tetraploidy, and sex chromosome abnormalities including but not limited to XO, XXY, XYY, and XXX.

In addition, target nucleic acids that can be analyzed according to the present invention comprise specific genetic loci such as genes or portions thereof (e.g., exons, introns, promoters or other regulatory regions). Table 1 lists non-limiting examples of such genes and associated genetic diseases, disorders or conditions. As understood by one of ordinary skill in the art, a gene may be known by more than one name. The listing in Table 1 does not exclude the existence of additional genes that may be associated with a particular disease. The present invention encompasses those additional genes including those that will be discovered in the future associated with each particular diseases.

TABLE 1

Exemplary genes associated with genetic diseases, disorders or conditions

| Disease, Disorder or condition | Gene | Protein Product |
| --- | --- | --- |
| Achondroplasia | FGFR3 | fibroblast growth factor receptor 3 |
| Adrenoleukodystrophy | ABCD1 | ATP-binding cassette (ABC) transporters |
| Alpha-1-antitrypsin deficiency | SERPINA1 | serine protease inhibitor |
| Alpha-thalassemia | HBA 1&2 | hemoglobin alpha 1&2 |
| Alport syndrome | COL4A5 | collagen, type IV, alpha 5 |
| Amyotrophic lateral sclerosis | SOD1 | superoxide dismutase 1 |
| Angelman syndrome | UBE3A | ubiquitin protein ligase E3A |
| Ataxia telangiectasia | ATM | ataxia telangiectasia mutated |
| Autoimmune polyglandular syndrome | AIRE | autoimmune regulator |
| Bloom syndrome | BLM, RECQL3 | recQ3 helicase-like |
| Burkitt lymphoma | MYC | v-myc myelocytomatosis viral oncogene homolog |
| Canavan disease | ASPA | aspartoacylase |
| Congenital adrenal hyperplasia | CYP21 | cytochrome P450, family 21 |
| Cystic fibrosis | CFTR | cystic fibrosis transmembrane conductance regulator |
| Diastrophic dysplasia | SLC26A2 | sulfate transporter |
| Duchenne muscular dystrophy | DMD | Dystrophin |
| Familial dysautonomia | IKBKAP | IKK complex-associated protein (IKAP) |
| Familial Mediterranean fever | MEFV | Mediterranean fever protein |
| Fanconi anemia | FANCA, FANCB (FAAP95), FANCC, FANCD1 (BRCA2), FANCD2, FANCE, FANCF, FANCG, FANCI, FANCJ (BRIP1), FANCL (PHF9 and POG), FANCM (FAAP250) | (proteins involved in DNA repair) |
| Fragile X syndrome | FMR1 | fragile X mental retardation 1 |
| Friedrich's ataxia | FRDA | Frataxin |
| Gaucher disease | GBA | glucosidase |
| Glucose galactose malabsorption | SGLT1 | sodium-dependent glucose cotransporter |
| Glycogen disease type I (GSDI) | G6PC (GSDIa) SLC37A4 (GSDIb) | glucose-6-phosphatase glucose-5-phosphate transporter 3, solute carrier family 37 member 4 |
| Gyrate atrophy | OAT | crnithine aminotransferase |
| Hemophilia A | F8 | hoagulation factor VIII |
| Hereditary hemocrhomatosis | HFE | hemochromatosis protein |
| Huntington disease | HD | Tuntingtin |
| Immunodeficiency with hyper-IgM | TNFSF5 | humor necrosis factor member 5 |
| Lesch-Nyhan syndrome | HPRT1 | hypoxanthine phosphoribotransferase |
| Maple syrup urine disease (MSUD) | BCKDHA | branched chain keto acid |
| Marfan syndrome | FBN1 | Fibrillin |
| Megalencephalic leukoencephalopathy | MLC1 | (putative transmembrane protein) |
| Menkes syndrome | ATP7A | ATPase Cu++ transporting |
| Metachromatic leukodystrophy (MLD) | ARSA | arylsulfatase A |
| Mucolipidosis IV (ML IV) | MCOLN1 | Mucolipin-1 |
| Myotonic dystrophy | DMPK | myotonic dystrophy protein kinase |
| Nemaline myopathy | | |
| Neurofibromatosis | NF1, NF2 | neurofibromin |
| Niemann Pick disease (types A and B type) | SMPD1 | sphingomyelin phosphodiesterase 1, acid lysosomal (acid sphingomyelinase) |
| Niemann Pick disease (type C) | NPC1, NPC2 | Niemann-Pick disease, type C1 (an integral membrane protein) and Niemann-Pick disease, type C2 |

TABLE 1-continued

Exemplary genes associated with genetic diseases, disorders or conditions

| Disease, Disorder or condition | Gene | Protein Product |
| --- | --- | --- |
| Paroxysmal nocturnal hemoglobinuria | PIGA | phosphatidylinositol glycan |
| Pendred syndrome | PDS | Pendrin |
| Phenylketonuria | PAH | phenylalanine hydroxylase |
| Refsum disease | PHYH | Phytanoyl-CoA hydroxylase |
| Retinoblastoma | RB | retinoblastoma 1 |
| Rett syndrome | MECP2 | methyl CpG binding protein |
| SCID-ADA (Severe combined immunodeficiency-ADA) | ADA | adenosine deaminase |
| SCID-X-linked (Sever combined immunodeficiency-X-linked) | IL2RG | Interleukin-2-receptor, gamma |
| Sickle cell anemia (also known as beta-thalassemia) | HBB | hemoglobin, beta |
| Spinal muscular atrophy (SMA) | SMN1, SMN2 | survival of motor neuron 1, survival of motor neuron 2 |
| Tangier disease | ABCA1 | ATP-binding cassette A1 |
| Tay-Sachs disease | HEXA | hexosaminidase |
| Usher syndrome (Also known as Hallgren syndrome, Usher-Hallgren syndrome, rp-dysacusis syndrome and dystrophia retinae dysacusis syndrome.) | MYO7A | myosin VIIA |
| | USH1C | Harmonin |
| | CDH23 | cadherin 23 |
| | PCDH15 | protocadherin 15 |
| | USH1G | SANS |
| | USH2A | Usherin |
| | GPR98 | VLGR1b |
| | DFNB31 | Whirlin |
| | CLRN1 | clarin-1 |
| Von Hippel-Lindau syndrome | VHL | elongin binding protein |
| Werner syndrome | WRN | Werner syndrome protein |
| Wilson's disease | ATP7B | ATPase, Cu++ transporting |
| Zellweger syndrome | PXR1 | peroxisome receptor 1 |

Thus, target loci that can be analyzed using inventive methods of the present invention include, but are not limited to, genes identified in Table 1, or a portion thereof (e.g., coding (e.g., exon) or non-coding (e.g., intron, or regulatory) region). The sequences of the genes identified in Table 1 are known in the art and are readily accessible by searching in public databases such as GenBank using gene names and such sequences are incorporated herein by reference.

Although most genes are normally present in two copies per genome equivalent, a large number of genes have been found for which copy number variations exist between individuals. Copy number differences can arise from a number of mechanisms, including, but not limited to, gene duplication events, gene deletion events, gene conversion events, gene rearrangements, chromosome transpositions, etc. Differences in copy numbers of certain genes may have implications including, but not limited to, risk of developing a disease or condition, likelihood of progressing to a particular disease or condition stage, amenability to particular therapeutics, susceptibility to infection, immune function, etc. In addition to the genes listed in Table 1, methods disclosed herein are suitable for analyzing copy numbers at loci with such copy number variants. The Database of Genomic Variants, which is maintained at the website whose address is "http://" followed immediately by "projects.tcag.ca/variation" (the entire contents of which are herein incorporated by reference in their entirety), lists more than at least 38,406 copy number variants (as of Mar. 11, 2009). (See, e.g., Iafrate et al. (2004) "Detection of large-scale variation in the human genome" *Nature Genetics*. 36(9): 949-51; Zhang et al. (2006) "Development of bioinformatics resources for display and analysis of copy number and other structural variants in the human genome." 115(3-4):205-14; Zhang et al. (2009) "Copy Number Variation in Human Health, Disease and Evolution," *Annual Review of Genomics and Human Genetics*. 10:451-481; and Wain et al. (2009) "Genomic copy number variation, human health, and disease." *Lancet*. 374:340-350, the entire contents of each of which are herein incorporated by reference).

Examples of diseases where the target sequence may exist in one copy in the maternal DNA (heterozygous) but can cause disease in a fetus (homozygous), include sickle cell anemia, cystic fibrosis, hemophilia, and Tay Sachs disease. Accordingly, using the methods described here, one may distinguish genomes with one mutation from genomes with two mutations. Sickle-cell anemia is an autosomal recessive disease. Nine-percent of US African Americans are heterozygous, while 0.2% are homozygous recessive. The recessive allele causes a single amino acid substitution in the beta chains of hemoglobin.

Tay-Sachs Disease is an autosomal recessive resulting in degeneration of the nervous system. Symptoms manifest after birth. Children homozygous recessive for this allele rarely survive past five years of age. Sufferers lack the ability to make the enzyme N-acetyl-hexosaminidase, which breaks down the GM2 ganglioside lipid.

Another example is phenylketonuria (PKU), a recessively inherited disorder whose sufferers lack the ability to synthesize an enzyme to convert the amino acid phenylalanine into tyrosine. Individuals homozygous recessive for this allele have a buildup of phenylalanine and abnormal breakdown products in the urine and blood.

Hemophilia is a group of diseases in which blood does not clot normally. Factors in blood are involved in clotting. Hemophiliacs lacking the normal Factor VIII are said to have Hemophilia A, and those who lack Factor IX have hemophilia B. These genes are carried on the X chromosome, so primers and probes may be used in the present method to detect whether or not a fetus inherited the mother's defective X chromosome, or the father's normal allele.

A listing of gene mutations for which the present method may be adapted is found at http://www.gdb.org/gdb, The GDB Human Genome Database, The Official World-Wide Database for the Annotation of the Human Genome Hosted by RTI International, North Carolina USA.

Sample Preparation

Any of a variety of biological samples may be suitable for use with methods disclosed herein. Generally, any biological samples containing nucleic acids (e.g., cells, tissue, etc.) may be used. Types of biological samples include, but are not limited to, cells, tissue, whole blood, plasma, serum, urine, stool, saliva, cord blood, chorionic villus samples amniotic fluid, and transcervical lavage fluid. Tissue biopsies of any type may also be used. Cell cultures of any of the above-mentioned biological samples may also be used in accordance with inventive methods, for example, chorionic villus cultures, amniotic fluid and/or amniocyte cultures, blood cell cultures (e.g., lymphocyte cultures), etc. In some embodiments, biological specimens comprise diseased cells such cancer or tumor cells.

In some embodiments, biological samples are prenatal samples. For example, a sample such as amniotic fluid, maternal blood, serum or plasma can be taken from a pregnant woman and can be assayed for according to the invention. The present method is particularly useful for non-invasive testing. In some embodiments, starting material is maternal peripheral venous blood.

Thus, a typical biological sample suitable for the present invention contain heterogeneous nucleic acids. In some embodiments, a biological sample contains a mixture of nucleic acids from different cell types (e.g., normal cells and diseased cells such as tumor cells). In some embodiments, a biological sample (e.g., blood, serum or plasma) contains a mixture of maternal nucleic acids and fetal nucleic acids. The present invention can be used to analyze a particular target chromosome or genetic locus present in diseased (e.g., cancer) or fetal cells.

In some embodiments, the present invention is used to detect target nucleic acids that are present as rare events in a biological sample. In some embodiments, the amount of target nucleic acids detected by an inventive method of the present invention represents less than 1% (e.g., less than 0.5%, 0.1%, 0.01%, 0.001%, 0.0001%) of the total nucleic acids in a biological sample. In some embodiments, the amount of target nucleic acids detected by an inventive method of the present invention represents less than 1 out of a million of the total nucleic acids in a biological sample. In some embodiments, the amount of target nucleic acids detected by an inventive method of the present invention represents less than 1 out of 10 million of the total nucleic acids in a biological sample.

The present invention is particularly useful for analyzing small amount of biological samples or specimens. In some embodiments, the present invention can be used to analyze a biological sample that contain total DNA less than 10,000 (e.g., less than 1,000, 100, 50, 25, 20, 15, 10, 5, 2) genomic equivalents. In some embodiments, the present invention can be used to analyze a biological sample that contain total DNA less than 1 genomic equivalent. Typically, fetal DNA is present as roughly 25 genome equivalents/ml of maternal plasma in early pregnancy, and a fetal DNA concentration is about 3.4% of total plasma DNA. Therefore, it is contemplated that 10-20 ml of maternal blood contains about at least 10,000 genome equivalents of total DNA. In some embodiments, a suitable biological sample contains about 20 ml, 15 ml, 10 ml, 5 ml, 4 ml, 3 ml, 2 ml, 1 ml, 0.5 ml, 0.1 ml, 0.01 ml, 0.001 ml of maternal blood.

It should be noted that, while the present description refers throughout to DNA, fetal RNA found in maternal blood may be analyzed as well. As described in Ng et al., "mRNA of placental origin is readily detectable in maternal plasma," Proc. Nat. Acad. Sci. 100(8): 4748-4753 (2003), hPL (human placental lactogen) and hCG (human chorionic gonadotropin) mRNA transcripts were detectable in maternal plasma. For example, mRNA encoding genes expressed in the placenta and present on the chromosome of interest can be used. For example, DSCR4 (Down syndrome critical region 4) is found on chromosome 21 and is mainly expressed in the placenta. Its mRNA sequence may be found at GenBank NM_005867. In this case, RNase H minus (RNase H—) reverse transcriptases (RTs) can be used to prepare cDNA for detection.

In some embodiments, the maternal blood may be processed to enrich the fetal DNA concentration, using various methods known in the art. Exemplary fetal DNA enrichment methods are described as follows.

Enrichment of DNA or RNA from Plasma

For example, circulatory DNA can be extracted from maternal plasma using commercial column technology (e.g., Roche High Pure Template DNA Purification Kit; Roche, Basel, Switzerland) in combination with a vacuum pump. After extraction, the DNA is separated by agarose gel (1%) electrophoresis (Invitrogen, Basel, Switzerland), and the gel fraction containing circulatory DNA with a size of approximately 300 bp is carefully excised. The DNA is extracted from this gel slice by using an extraction kit (QIAEX II Gel Extraction Kit; Qiagen, Basel, Switzerland) and eluted into a final volume of 40 µL sterile 10-mM trishydrochloric acid, pH 8.0 (Roche).

DNA may be concentrated by known methods, including centrifugation and various enzyme inhibitors. The DNA is bound to a selective membrane (e.g., silica) to separate it from contaminants. The DNA is preferably enriched for fragments circulating in the plasma, which are less than 1000 base pairs in length, generally less than 300 bp. This size selection may be done on a DNA size separation medium, such as an electrophoretic gel or chromatography material. Such a material is described in Huber et al., "High-resolution liquid chromatography of DNA fragments on non-porous poly(styrene-divinylbenzene) particles," Nucleic Acids Res. 1993 Mar. 11; 21(5): 1061-1066, gel filtration chromatography, TSK gel, as described in Kato et al., "A New Packing for Separation of DNA Restriction Fragments by High Performance Liquid Chromatography," J. Biochem, 1984, Vol. 95, No. 1 83-86. Or, other methods of enriching for DNA fragments of a particular size may be used.

In addition, enrichment may be accomplished by suppression of certain alleles through the use of peptide nucleic acids (PNAs), which bind to their complementary target sequences, but do not amplify.

Plasma RNA extraction is described in Enders et al., "The Concentration of Circulating Corticotropin-releasing Hormone mRNA in Maternal Plasma Is Increased in Preeclampsia," Clinical Chemistry 49: 727-731, 2003. As described there, plasma harvested after centrifugation steps is mixed Trizol LS reagent (Invitrogen) and chloroform. The mixture is centrifuged, and the aqueous layer transferred to new tubes. Ethanol is added to the aqueous layer. The mixture is then applied to an RNeasy mini column (Qiagen) and processed according to the manufacturer's recommendations. Or, other RNA extraction methods accepted in the art may be used.

Blood—Extraction from Fetal Cells

Fetal DNA may be enriched by methods known in the art. For example, United States Patent Application 20040137470 to Dhallan, Ravinder S, published Jul. 15, 2004, entitled "Methods for detection of genetic disorders," and incorporated by reference in its entirety herein, describes an enrichment procedure for fetal DNA, in which blood is collected into 9 ml EDTA Vacuette tubes (catalog number NC9897284) and 0.225 ml of 10% neutral buffered solution containing formaldehyde (4% w/v), is added to each tube, and each tube gently is inverted. The tubes are stored at 4° C. until ready for processing.

Agents that impede cell lysis or stabilize cell membranes can be added to the tubes. Such agents may include but are not limited to, formaldehyde, and derivatives of formaldehyde, formalin, glutaraldehyde, and derivatives of glutaraldehyde, crosslinkers, primary amine reactive crosslinkers, sulfhydryl reactive crosslinkers, sulfhydryl addition or disulfide reduction, carbohydrate reactive crosslinkers, carboxyl reactive crosslinkers, photoreactive crosslinkers, cleavable crosslinkers, and the like. Any concentration of agent that stabilizes cell membranes or impedes cell lysis can be added. In a preferred embodiment, the agent that stabilizes cell membranes or impedes cell lysis is added at a concentration that does not impede or hinder subsequent reactions.

Flow cytometry techniques can also be used to enrich fetal cells (see e.g., Herzenberg et al., PNAS 76: 1453-1455 (1979); Bianchi et al., PNAS 87: 3279-3283 (1990); Bruch et al., Prenatal Diagnosis 11: 787-798 (1991) incorporated by reference herein). U.S. Pat. No. 5,432,054 also incorporated by reference in its entirety herein, describes a technique for separation of fetal nucleated red blood cells, using a tube having a wide top and a narrow, capillary bottom made of polyethylene. Centrifugation using a variable speed program results in a stacking of red blood cells in the capillary based on the density of the molecules. The density fraction containing low-density red blood cells, including fetal red blood cells, is recovered and then differentially hemolyzed to preferentially destroy maternal red blood cells. A density gradient in a hypertonic medium is used to separate red blood cells, now enriched in the fetal red blood cells from lymphocytes and ruptured maternal cells. The use of a hypertonic solution shrinks the red blood cells, which increases their density, and facilitates purification from the more dense lymphocytes. After the fetal cells have been isolated, fetal DNA can be purified using standard techniques in the art.

Further, an agent that stabilizes cell membranes may be added to the maternal blood to reduce maternal cell lysis. Such agents may include, but are not limited to, aldehydes, urea formaldehyde, phenol formaldehyde, DMAE (dimethylaminoethanol), cholesterol, cholesterol derivatives, high concentrations of magnesium, vitamin E, and vitamin E derivatives, calcium, calcium gluconate, taurine, niacin, hydroxylamine derivatives, bimoclomol, sucrose, astaxanthin, glucose, amitriptyline, isomer A hopane tetral phenylacetate, isomer B hopane tetral phenylacetate, citicoline, inositol, vitamin B, vitamin B complex, cholesterol hemisuccinate, sorbitol, calcium, coenzyme Q, ubiquinone, vitamin K, vitamin K complex, menaquinone, zonegran, zinc, *Ginkgo biloba* extract, diphenylhydantoin, perftoran, polyvinylpyrrolidone, phosphatidylserine, tegretol, PABA, disodium cromglycate, nedocromil sodium, phenyloin, zinc citrate, mexitil, dilantin, sodium hyaluronate, or polaxamer 188.

An example of a protocol for using this agent is as follows: The blood is stored at 4° C. until processing. The tubes are spun at 1000 rpm for ten minutes in a centrifuge with braking power set at zero. The tubes are spun a second time at 1000 rpm for ten minutes. The supernatant (the plasma) of each sample is transferred to a new tube and spun at 3000 rpm for ten minutes with the brake set at zero. The supernatant is transferred to a new tube and stored at −80° C. Approximately two milliliters of the "buffy coat," which contains maternal cells, is placed into a separate tube and stored at −80° C.

Plasma-Free Fetal DNA

Genomic DNA may be isolated from the plasma using the Qiagen Midi Kit for purification of DNA from blood cells, following the manufacturer's instructions (QIAmp DNA Blood Midi Kit, Catalog number 51183). DNA is eluted in 100 µl of distilled water. The Qiagen Midi Kit also is used to isolate DNA from the maternal cells contained in the "buffy coat."

Finally, it is noted that, in certain embodiments, one may also use samples from tissue, saliva, urine, tear, vaginal secretion, breast fluid, breast milk, or sweat.

Whole Genome Amplification

In some embodiments, the total DNA in a biological sample is first amplified using whole genome amplification (WGA) methods. Various WGA methods are known in the art and can be used in the present invention. Exemplary methods are described in U.S. Application Publication Nos. 20030082559 and 20030104431, which are incorporated by reference herein.

In some embodiments, nucleic acid samples are randomly fragmented, then treated such that the ends of the different fragments all contain the same DNA sequence. Fragments with universal ends can then be amplified in a single reaction with a single pair of amplification primers. Exemplary methods for fragmentation and end treatment are described in the "Bridge PCR Amplification" section below. Various other methods are known in the art and can be used in the present invention.

Single Molecule Amplification

The term "single molecule amplification" is used herein to distinguish from high density multi-molecule amplification reactions known in the art. Single molecule amplification typically involves first separating or arranging nucleic acid molecules obtained from a biological sample to form a plurality of amplification sites and wherein each amplification site contains on average one nucleic acid molecule; and amplifying each individual nucleic acid molecule in the amplification site to generate amplified products. Typically, amplified products form clusters that can be individually resolved. The term "individually resolved" is used herein to indicate that, when visualized, it is possible to distinguish one cluster from its neighboring cluster. Visualization may be effected by the use of labeled probes that can be hybridized to the clusters. In some embodiments, clusters containing amplified products are generated by polymerase reactions. Such clusters are also known as polonies or nucleic acid clones or colonies. Polymerase based amplification methods include, but are not limited to, polymerase chain reactions (PCRs) and strand displacement amplification (e.g., rolling circle amplification). Various other amplification methods are known in the art and can be used for the present invention. Additional exemplary methods for amplification include, but are not limited to, self-sustained sequence reaction, ligase chain reaction, rapid amplification of cDNA ends, ligase chain reaction, Q-beta phage amplification, and splice overlap extension.

In some embodiments, nucleic acids can be separated and amplified on solid supports. Solid support suitable for the invention can be any solid surface to which nucleic acids can be covalently attached, such as for example latex beads, dextran beads, polystyrene, polypropylene surface, polyacrylamide gel, gold surfaces, glass surfaces and silicon wafers. In some embodiments, solid support is a glass surface.

Means for attaching nucleic acids to a solid support as used herein refers to any chemical or non-chemical attachment method including chemically-modifiable functional groups. "Attachment" relates to immobilization of nucleic acid on solid supports by either a covalent attachment or via irreversible passive adsorption or via affinity between molecules (for example, immobilization on an avidin-coated surface by biotinylated molecules). Typically, the attachment is of sufficient strength that it cannot be removed by washing with water or aqueous buffer under DNA-denaturing conditions. "Chemically-modifiable functional group" as used herein refers to a group such as for example, a phosphate group, a carboxylic or aldehyde moiety, a thiol, or an amino group.

For example, a collection of nucleic acid molecules can be distributed on a surface of solid support such that individual molecules can be attached to a discrete site. Solid phase supports suitable for use with the invention may have a wide variety of forms, including microparticles; beads, membranes, slides, plates micromachined chops, tubes and the like. Solid phase supports of the invention may be made of a wide variety of materials, including, but not limited to, glass, plastic, silicon, alkanethiolate-dervatized gold, cellulose, low cross-linked and high cross-linked polystyrene, silica gel, polyamide, optical fiber, plastics, and the like. In some embodiments, the collection of nucleic acid molecules can be separated using flowcell technology.

In some embodiments, nucleic acids can be separated and amplified in semi-solid or liquid phase. For example, the collection of nucleic acid molecules can be distributed within a gel matrix (e.g., agarose gel matrix). In some embodiments, the collection of nucleic acid molecules can be mixed with emulsion beads.

In some embodiments, capturing oligonucleotides are immobilized on the solid or semi-solid support to facilitate capturing and immobilization of individual nucleic acid molecules (e.g., polypeptides). In some embodiments, capturing oligonucleotides can contain sequences complementary to a universal sequence present on nucleic acid template molecules, such as a tag or an adaptor sequence. For example, nucleic acid molecules in a biological sample can be first treated to attach a tag or adaptor sequence at the 5' and/or 3' end and the tag or adaptor sequences can bind to the capturing oligonucleotides immobilized on the solid or semi-solid supports. In some embodiments, one or more capturing sequences can be used.

In some embodiments, suitable capturing oligonucleotides can hybridize to the tag or adaptor sequences under suitable conditions according to the invention (e.g., high stringent conditions). Exemplary capturing oligonucleotides can contain various numbers of nucleotides. For example, suitable oligonucleotides may contain 1-50 nucleotides (e.g., 3-40, 3-30, 3-20, 30-15, 3-10, 6-40, 6-30, 6-20, 6-10, 8-30, 8-20, 8-15, 10-30, 10-20, 10-15 nucleotides). In some embodiments, suitable oligonucleotides may contain 1, 2, 3, 6, 8, 10, 12, 14, 16, 18, 20, 25, 30, 35, 40, 45, or 50 nucleotides. Various methods are known in the art for design and synthesize suitable capturing oligonucleotides and such methods are well within skills of ordinary artisan. In some embodiments, capturing oligonucleotides can also be used as PCR primers for amplification (see the "Bridge PCR Amplification" section). Thus, capturing oligonucleotides are also referred to as colony primers.

Capturing oligonucleotides may be used with the solid phase support that they are synthesized on, or they may be separately synthesized and attached to a solid phase support for use, e.g. as disclosed by Lund et al. Nucleic Adds Research, 16: 10861-10880 (1988); Albretsen et al, Anal. Biochem., 189: 40-50 (1990); Wolf et al, Nucleic Acids Research, 15: 2911-2926 (1987); or Ghosh et al, Nucleic Acids Research, 15: 5353-5372 (1987) all of which are incorporated by reference herein.

In some embodiments, the attachment of the capturing oligonucleotides and nucleic acid template to the solid support is thermostable at the temperature to which the support may be subjected to during the nucleic acid amplification reaction, for example temperatures of up to approximately 100° C., for example approximately 94° C. In some embodiments, the attachment is covalent in nature. In further embodiments, the covalent binding of the capturing oligonucleotides and nucleic acid template(s) to the solid support is induced by a crosslinking agent such as for example 1-ethyl-3-(3-dimethylaminopropyl)-carbodiimide hydrochloride (EDC), succinic anhydride, phenyldiisothiocyanate or maleic anhydride, or a hetero-bifunctional crosslinker such as for example m-maleimidobenzoyl-N-hydroxysuccinimide ester (MBS), N-succinimidyl[4-iodoacethyl]aminobenzoate (SIAB), Succinimidyl 4-[N-maleimidomethyl] cyclohexane-1-carboxylate (SMCC), N-y-maleimidobutyryloxy-succinimide ester (GMBS), Succinimidyl-4-[p-maleimidophenyl]butyrate (SMPB) and the sulfo (water-soluble) corresponding compounds.

In some embodiments, a solid support suitable for the invention has a derivatised and/or functionalized surface. In some embodiments, the derivatised surface of the solid support is subsequently modified with bifunctional crosslinking groups to provide a functionalized surface, preferably with reactive crosslinking groups. "Derivatised surface" as used herein refers to a surface which has been modified with chemically reactive groups, for example amino, thiol or acrylate groups. "Functionalized surface" as used herein refers to a derivatised surface which has been modified with specific functional groups, for example the maleic or succinic functional moieties.

In some embodiments, the attachment of capturing oligonucleotides should not be affected by either the exposure to high temperatures and the repeated heating/cooling cycles employed during the nucleic acid amplification procedure. Moreover, in alternate embodiments, the support should allow the obtaining of a density of attached capturing oligonucleotides (or colony primers) of at least 1 fmol/mm$^2$ (e.g., at least 10 fmol/mm$^2$, at least 20 fmol/mm$^2$, at least 30 fmol/mm$^2$, at least 40 fmol/mm$^2$, at least 50 fmol/mm$^2$).

A suitable support should have a uniformly flat surface with low fluorescence background and should also be thermally stable (non-deformable). Solid supports, which allow the passive adsorption of DNA, as in certain types of plastic and synthetic nitrocellulose membranes, may not be suitable for certain applications. Finally, the solid support should be disposable, thus should not be of a high cost.

In some embodiments, the invention is implemented with microparticles or beads uniformly coated (i.e., having a coating that is substantially uniform) with capturing oligonucleotides. Microparticle supports and methods of covalently or noncovalently linking oligonucleotides to their surfaces are well known, as exemplified by the following references: Beaucage and Iyer (cited above); Gait, editor, Oligonucleotide Synthesis: A Practical Approach (IRL Press, Oxford, 1984); and the references cited above. Generally, the size and shape of a microparticle is not critical; however, microparticles in the size range of a few, e.g. 1-2, to several hundred, e.g. 200-1000 μm diameter are preferable, as they facilitate the construction and manipulation of large repertoires of oligonucleotide tags with minimal reagent and sample usage.

In some embodiments, commercially available controlled-pore glass (CPG) or polystyrene supports are employed as solid phase supports in the invention. Such supports come available with base-labile linkers and initial nucleosides attached, e.g. Applied Biosystems (Foster City, Calif.). In some embodiments, microparticles having pore sizes between 500 and 1000 angstroms are employed.

Other capturing moieties can be used in methods according to the invention. For example, streptavidin can be attached to supports and the nucleic acids can be biotinylated such that streptavidin can bind biotinylated nucleic acid molecules.

Bridge PCR Amplification

In some embodiments, bridge PCR amplification can be used for single molecule amplification according to the invention. Typically, bridge PCR involves universal amplification reaction, whereby a DNA sample is randomly fragmented, then treated such that the ends of the different fragments all contain the same DNA sequence. Fragments with universal ends can then be amplified in a single reaction with a single pair of amplification primers. Separation of the collection of fragments to the single molecule level prior to amplification ensures that the amplified molecules form discrete populations that can then be further analyzed. Such separations can be performed either in emulsions, on a surface, or within a gel.

In some embodiments, the nucleic acids to be amplified are first obtained in double stranded form. When the nucleic acid is provided in single stranded form, for example mRNA, it is first made into a double stranded form by means well known and documented in the art, for example, using oligo-dT primers and reverse transcriptase and DNA polymerase. The nucleic acids to be used in the method of the invention can be of variable lengths. For example, they can be at least 50 base pairs in length. In some embodiments, they can be 150 to 4000 base pairs in length. Various methods known in the art can be used to prepare appropriate nucleic acid fragments such as, for example, shot gun methods, restriction enzyme digestion, and others.

In some embodiments, two universal adapter or tag sequences are attached to the 5' and 3' end of individual nucleic acid fragment. This can be done using methods which are well known and documented in the art, for example by ligation, or by inserting the nucleic acid to be amplified into a biological vector at a site which is flanked by the appropriate oligonucleotide sequences.

The adaptor sequence attached at the 5' end of the nucleic acid can be of any sequence and any length and is denoted herein as sequence A5'. The oligonucleotide sequence attached at the 3' end of the nucleic acid can be of any sequence and any length and is denoted herein as sequence A3'. Suitable lengths and sequences of adaptor oligonucleotide can be selected using methods well known and documented in the art. For example the oligonucleotide sequences attached to each end of the nucleic acid to be amplified are normally relatively short nucleotide sequences of between 5 and 100 nucleotides in length (e.g., 5-50, 5-40, 5-30, 5-25, 5-20, 5-15, 10-50, 10-40, 10-30, 10-25, 10-20, 15-30, or 15-25 nucleotides or other ranges within this range).

In some embodiments, the sequence of the 3' end adaptor A3' is such that it can hybridize to one of the capturing oligonucleotides (X). In some embodiments, the sequence of the 5' end adaptor A5' is such that it is the same as one of the capturing oligonucleotides (X). In some embodiments, the sequence of the 3' end adaptor A3' is complementary to the sequence of the 5' end adaptor A5'. The adaptor oligonucleotide sequences of the invention may be prepared using techniques which are standard or conventional in the art, or may be purchased from commercial sources.

In some embodiments, the 5' end of the nucleic acid fragment prepared as described herein is modified to carry a means for attaching the nucleic acid fragment covalently to a solid support. Such a means can be, for example, a chemically modifiable functional group, such as, for example a phosphate group, a carboxylic or aldehyde moiety, a thiol, or an amino group.

The capturing oligonucleotides (also known as colony primers) of the invention may be prepared using techniques that are standard or conventional in the art. Generally, the capturing oligonucleotides of the invention will be synthetic oligonucleotides generated by methods well known and documented in the art or may be purchased from commercial sources. According to the method of the invention, one or two different colony primers X, can be used to amplify any nucleic acid sequence.

Typically, capturing oligonucleotides are immobilized to a support by the 5' end leaving its 3' end remote from the support such that the capturing oligonucleotide is available for chain extension by a polymerase once hybridization with a complementary oligonucleotide sequence contained at the 3' end of the nucleic acid template has taken place.

In some embodiments, the nucleic acid templates and colony primers of the invention are used in appropriate proportions so that when they are attached to the solid support an appropriate density of attached nucleic acid templates and colony primers is obtained. In some embodiments, the proportion of colony primers in the mixture is higher than the proportion of nucleic acid templates. In some embodiments, the ratio of colony primers to nucleic acid templates is such that when the colony primers and nucleic acid templates are immobilized to the solid support a "lawn" of colony primers is formed comprising a plurality of colony primers being located at an approximately uniform density over the whole or a defined area of the solid support, with individual nucleic acid templates being immobilized at intervals within the lawn of colony primers.

The nucleic acid templates may be provided in single stranded form. For example, before attaching the nucleic acid template to the solid support, it can be made into a single stranded form using methods which are well known and documented in the art, for example by heating to approximately 94° C. and quickly cooling on ice. However, they may also be provided totally or partly in double stranded form, either with one 5' end or both 5' ends modified so as to allow attachment to the support. In that case, after completion of the attachment process, the two strands can be separated by means known in the art, e.g. by heating to 94° C., before washing the released strands away. It will be appreciated that in the case where both strands of the double stranded molecules have reacted with the surface and are both attached, the result will be the same as in the case when only one strand is attached and one amplification step has been performed. In other words, in the case where both strands of a double stranded template nucleic acid have been attached, both strands are necessarily attached close to each other and are indistinguishable from the result of attaching only one strand and performing one amplification step. Thus, single stranded and double stranded template nucleic acids might be used for providing template nucleic acids attached to the surface and suitable for colony generation.

The distance between the individual colony primers and the individual nucleic acid templates (and hence the density of the colony primers and nucleic acid templates) can be controlled by altering the concentration of colony primers and nucleic acid templates that are immobilized to the support. In some embodiments, a suitable density of colony primers is at least 1 fmol/mm$^2$ (e.g., at least 10 fmol/mm$^2$, at least 20 fmol/mm$^2$, at least 30 fmol/mm$^2$, at least 40 fmol/mm$^2$, at least 50 fmol/mm$^2$). In some embodiments, a suitable density of colony primers is at least between 30 to 60 fmol/mm$^2$. The density of nucleic acid templates for use in the method of the invention is typically 10,000/mm$^2$ to 10,000,000/mm$^2$ (e.g., between 10,000/mm$^2$ to 1,000,000/mm$^2$, 10,000/mm$^2$ to 100,000/mm$^2$, 100,000/mm$^2$ to 10,000,000/mm$^2$, 100,000/mm$^2$ to 1,000,000/mm$^2$. Or, ranges within these ranges, or ranges encompassing these ranges may be used.

Controlling the density of attached nucleic acid templates and colony primers in turn allows the final density of nucleic acid colonies on the surface of the support to be controlled. This is due to the fact that according to the method of the invention, one nucleic acid colony can result from the attachment of one nucleic acid template, providing the colony primers of the invention are present in a suitable location on the solid support. The density of nucleic acid molecules within a single colony can also be controlled by controlling the density of attached colony primers. In some embodiments, the density of colonies can be determined based on the detection methods (e.g., the probe numbers, the detection signals and the resolution of the detection methods (e.g., camera resolution etc.)). One of skill in the art can readily determine the desirable density based on relevant parameters.

In some embodiments, suitable density of colonies provides colony numbers that are sufficiently large to permit hybridization by multiplexed target and/or reference-specific probes and provide sufficient detectable colony counts that allows statistically significantly analysis. In some embodiments, a suitable density of colonies comprises up to 1,000,000 (e.g., up to 800,000, 600,000, 400,000, 200,000, 100,000) detectable colony counts.

Once the colony primers and nucleic acid templates of the invention have been immobilized on the solid support at the appropriate density, nucleic acid colonies of the invention can then be generated by carrying out an appropriate number of cycles of amplification on the covalently bound template nucleic acid so that each colony comprises multiple copies of the original immobilized nucleic acid template and its complementary sequence. One cycle of amplification consists of the steps of hybridization, extension and denaturation and these steps are generally performed using reagents and conditions well known in the art for PCR.

A typical amplification reaction comprises subjecting the solid support and attached nucleic acid template and colony primers to conditions which induce primer hybridization, for example subjecting them to a temperature of around 65° C. Under these conditions the oligonucleotide sequence A3' at the 3' end of the nucleic acid template will hybridize to the immobilized colony primer X and in the presence of conditions and reagents to support primer extension, for example a temperature of around 72° C., the presence of a nucleic acid polymerase, for example, a DNA dependent DNA polymerase or a reverse transcriptase molecule (i.e., an RNA dependent DNA polymerase), or an RNA polymerase, plus a supply of nucleoside triphosphate molecules or any other nucleotide precursors, for example modified nucleoside triphosphate molecules, the colony primer will be extended by the addition of nucleotides complementary to the template nucleic acid sequence.

Examples of nucleic acid polymerases which can be used in the present invention are DNA polymerase (Klenow fragment, T4 DNA polymerase), heat-stable DNA polymerases from a variety of thermostable bacteria (such as Taq, VENT, Pfu, Tfl DNA polymerases) as well as their genetically modified derivatives (TaqGold, VENTexo, Pfu exo). A combination of RNA polymerase and reverse transcriptase can also be used to generate the amplification of a DNA colony. Typically, the nucleic acid polymerase used for colony primer extension is stable under PCR reaction conditions, i.e., repeated cycles of heating and cooling, and is stable at the denaturation temperature used, usually approximately 94° C. In some embodiments, the DNA polymerase used is Taq DNA polymerase.

In some embodiments, the nucleoside triphosphate molecules used are deoxyribonucleotide triphosphates, for example dATP, dTTP, dCTP, dGTP, or are ribonucleoside triphosphates for example dATP, dUTP, dCTP, dGTP. The nucleoside triphosphate molecules may be naturally or non-naturally occurring.

After the hybridization and extension steps, on subjecting the support and attached nucleic acids to denaturation conditions two immobilized nucleic acids will be present, the first being the initial immobilized nucleic acid template and the second being a nucleic acid complementary thereto, extending from one of the immobilized colony primers X. Both the original immobilized nucleic acid template and the immobilized extended colony primer formed are then able to initiate further rounds of amplification on subjecting the support to further cycles of hybridization, extension and denaturation. Such further rounds of amplification will result in a nucleic acid colony comprising multiple immobilized copies of the template nucleic acid and its complementary sequence.

The initial immobilization of the template nucleic acid means that the template nucleic acid can only hybridize with colony primers located at a distance within the total length of the template nucleic acid. Thus the boundary of the nucleic acid colony formed is limited to a relatively local area to the area in which the initial template nucleic acid was immobilized. Clearly, once more copies of the template molecule and its complement have been synthesized by carrying out further rounds of amplification, i.e., further rounds of hybridization, extension and denaturation, then the boundary of the nucleic acid colony being generated will be able to be extended further, although the boundary of the colony formed is still limited to a relatively local area to the area in which the initial nucleic acid template was immobilized. Appropriate rounds of cycles can be determined based on the amount of the starting material, hybridization and/or detection methods (e.g., the probe numbers, the detection signals and the resolution of the detection methods (e.g., camera resolution etc.)). One of skill in the art can readily determine the desirable cycle rounds based on relevant parameters. In some embodiments, up to 35 (e.g., up to 34, 33, 32, 31, 30, 29, 28, 27) cycles are used.

Typically, the amplified product provides a pre-determined level of genomic equivalence. In some embodiments, the amplification generates up to 100,000 (e.g., up to 50,000, 40,000, 30,000, 20,000, 10,000) genomic equivalence.

Various modifications of bridge amplification are possible and known in the art. For example, various bridge amplification methods are described in U.S. Pat. No. 7,115,400, U.S. Publication No. 20090226975, and Bing D. H. et al. "Bridge Amplification: A Solid Phase PCR System for the Amplification and Detection of Allelic Differences in Single Copy Genes," Seventh International Symposium on Human Identification available on the internet at the Promega website, all of which are hereby incorporated by reference.

Bead Emulsion PCR

Emulsion PCR can be used to generate small beads with clonally amplified DNA, i.e., each bead contains one type of amplicon generated from single molecule template by PCR. Exemplary emulsion PCR are described in Dressman et al, Proc. Natl. Acad. Sci. USA. 100, 8817 (Jul. 22, 2003)) and Dressman et al. PCT publication WO2005010145, "METHOD AND COMPOSITIONS FOR DETECTION AND ENUMERATION OF GENETIC VARIATIONS," published 2005, Jan. 3, and hereby incorporated by reference for its description of a bead-based process to generate clonally amplified DNA.

For example, beads coated with capturing oligonucleotides (or colony primers) may be mixed with nucleotides with complementary adaptor or tag sequences. An aqueous mix containing all the necessary components for PCR plus primer-bound beads and template DNA may then be stirred together with an oil/detergent mix to create microemulsions. The aqueous compartments (which may be illustrated as small droplets in an oil layer) will generally contain an average of <1 template molecule and <1 bead. Different templates (control and test) may be pictured in one or less droplets to represent two template molecules whose sequences differ by one or many nucleotides. The microemulsions are temperature cycled as in a conventional PCR. If a DNA template and a bead are present together in a single aqueous compartment, the bead bound oligonucleotides act as primers for amplification.

Beads made of various materials and in various size can be used for the present invention. For example, suitable beads can be magnetic beads, plastic beads, gold particles, cellulose particles, polystyrene particles, to name but a few. Suitable beads can be microparticles in the size range of a few, e.g. 1-2, to several hundred, e.g. 200-1000 μn diameter. In some embodiments, commercially available controlled-pore glass (CPG) or polystyrene supports are employed as solid phase supports in the invention. Such supports come available with base-labile linkers and initial nucleosides attached, e.g. Applied Biosystems (Foster City, Calif.). In some embodiments, microparticles having pore sizes between 500 and 1000 angstroms are employed.

Oligonucleotides can be coupled to beads using various methods in the art. Exemplary methods for bridge amplification can be used to coupling oligonucleotides to beads. As additional non-limiting example, magnetic beads can be covalently bound to streptavidin (commercially available from Dynal Biotech, Inc. (650.01; Lake Success, N.Y.)) Beads are can be washed then suspended in Bind and Wash Buffer (BWB) (5 mMTris-HCl, 0.5 mM EDTA, 1.0 MNaCl, pH 7.5). Beads can then be incubated in BWB for 30 min at room temperature in the presence of 10 mM oligonucleotides. These oligonucleotides may then be modified with a dual biotin group at the 5' end with the biotin groups separated by a six-carbon linker (IDT; Coralville, Iowa). After binding, the beads may then be washed to thoroughly remove unbound oligonucleotides.

As non-limiting example, microemulsions for PCR can be prepared in an oil phase that is composed of 4.5% Span 80 (S6760; Sigma, St. Louis, Mo.), 0.40% Tween 80 (Sigma; S-8074), and 0.05% Triton X-100 (Sigma; T-9284) in mineral oil (Sigma; M-3516). The aqueous phase may consist of 67 mMTris-HCl (pH 8.8), 16.6 mM NH4S04, 6.7 mMMgCl2, 10 mM (3-mercaptoethanol, 1 mMdATP, 1 mMdCTP, 1 mMdGTP, 1 mMdTTP, 0.05 μM forward primer, 25 μM reverse primer, 45 units Platinum Taq (Invitrogen; 10966-034), various amounts of template DNA, and ~108 oligonucleotide-coupled beads in a total volume of 300 μl.

As a non-limiting example, water-in-oil microemulsions can be prepared by drop wise addition of 200 microliters of the aqueous phase to 400 microliters of the oil phase previously placed in a 2 ml round bottom cryogenic vial (430661; Corning, Corning, N.Y.). The drop wise addition is performed over-one minute while the mixture is being stirred at 1400 RPM with a magnetic microstir bar (58948-353; VWR, Plainfield, N.J.) on a VWR model 565 Magnetic Stirrer. After the addition of the aqueous phase, the mixture continued to be stirred for a total time of 30 minutes. Two emulsions may be made at once by placing two tubes in a rack placed at the center of the magnetic stirrer.

As a non-limiting example, for PCR cycling, the emulsions can be aliquotted into, e.g., 96 well PCR plate (e.g., each containing 100 μl). PCR can be carried out under usual conditions. For example, the PCR protocol may be as follows: 94° C. for 2 minutes; 40 cycles of 94° C. for 15 seconds, 57° C. for 30 seconds, 70° C. for 30 seconds. Or, similar protocols may be used.

Hybridization

Various methods can be used to analyze the amplified nucleic acids to detect and/or enumerate target nucleic acid molecules. In some embodiments, the present invention utilizes hybridization-based approach. For example, probes specific to target nucleic acids can be used to hybridize nucleic acid colonies, in situ, to identify nucleic acid colonies containing a target nucleic acid sequence, or a portion thereof. Typically, the probes are labeled with detectable signals such that the number of colonies containing a target nucleic acid sequence, or a portion thereof can be determined. In some embodiments, probes specific to a reference nucleic acids can be used to hybridize nucleic acid colonies, in situ, to identify nucleic acid colonies containing a reference nucleic acid sequence, or a portion thereof. Typically, the probes specific to the reference nucleic acid are labeled with distinctly detectable signals such that the number of colonies a reference nucleic acid sequence, or a portion thereof can be determined in parallel. In some embodiments, the relative amount of the target nucleic acids can be determined by comparing the first number of the colonies containing the target nucleic acid sequences to the second number of the colonies containing the reference nucleic acid sequences.

Alternatively or additionally, colonies containing amplified nucleic acids can be harvested and analyzed with array-based hybridization. Suitable arrays may contain probes that are specific to the target nucleic acids or portions thereof and/or probes that are specific to a reference nucleic acids or portions thereof.

Probe Design

Suitable probes are specific to the nucleic acids of interest (e.g., target or reference chromosomes or genes). The term "specific" when used in connection with a hybridization probe refers to a probe that can bind to its target under stringent conditions but not to other regions.

Probes for specific chromosome or genes (including specific disease forms) are prepared on the basis of nucleotide sequences associated with the chromosomes or genes of interest. The sequences of specific chromosomes or genes can be obtained from databases such as GenBank, EMBL and the like. Suitable probes typically are of a length that is large enough to hybridize specifically with its target but not so large as to impede the hybridization process. In alternate embodiments, suitable probes contain about 10-70 nucleotides (e.g., 10-60, 10-50, 10-40, 10-30, 10-25, 10-20, 15-70, 15-60, 15-50, 15-40, 15-30, 15-25, 20-70, 20-60, 20-50, 20-40, 20-30 nucleotides). Or, ranges within these ranges may be used. Various methods and software available in the art can be used to design specific probes.

There are more than 1,000 chromosome 21 specific PCR primer sets listed at the NIH UniSTS web site, which can be located at http://www.ncbi.nlm.nih.gov/entrez/query.fcgi?db=unists and found with the search phrase "human[organism] AND 21[chr]." UniSTS is a comprehensive database of sequence tagged sites (STSs) derived from STS-based maps and other experiments. STSs are associated with additional information such as genomic position, genes, and sequences. Similarly, primer sequences for other human chromosomes can be found by appropriately modifying the search query. These chromosome specific primers can be used to design chromosome specific probes suitable for the present invention.

Other chromosome specific primers are disclosed in United States Patent Application 20050164241 to Hahn, Sinuhe, et al., published Jul. 28, 2005, entitled "Non-invasive detection of fetal genetic traits," hereby incorporated by reference in its entirety.

Probes can also be derived from fragments of chromosome DNA that were isolated, purified, and amplified. For example, human genome can be broken into fragments using sequence-specific endonucleases or short gun approach and appropriate size of fragments can be isolated using size-exclusive chromatography to prepare probes. In some embodiments, probes can be derived from BACs, clonal populations of bacteria that maintain a single artificial chromosome. The artificial chromosomes (BAC) can be grown, extracted, and labeled.

In some embodiments, probes are designed based on a single locus. In some embodiments, probes are designed based on multiple genes or loci on a same chromosome. Although a single probe can be used in the present invention, in many embodiments, multiplexed probes are designed. Multiplexed probes provide robust signals and more accurate detection of the nucleic acids of interest. Appropriate level of multiplicity can be determined based on the size of the nucleic acids of interest (e.g., target or reference), the amount of starting materials and the desirable level of detectable counts for statistic analysis. In alternate embodiments, multiplexed probes contain 2-10,000 probes (e.g., 10-10,000, 10-5,000, 10-1,000, 10-500, 10-250, 10-100, 10-50 probes). In some embodiments, multiplexed probes contain about 10, 100, 200, 300, 400, 500, 1,000, 5,000, 10,000 probes. In some embodiments, same numbers of probes are used for the target nucleic acids and the references nucleic acids. In some embodiments, different numbers of probes are used for the target nucleic acids and the reference nucleic acids.

Probes can be tagged directly with various detectable moieties such as fluorophores. Tagging can be done in various ways, such as nick translation, or PCR using tagged nucleotides.

Detectable Entities

Any of a wide variety of detectable agents can be used in the practice of the present invention. Suitable detectable agents include, but are not limited to: various ligands, radionucleotides; fluorescent dyes; chemiluminescent agents (such as, for example, acridinum esters, stabilized dioxetanes, and the like); bioluminescent agents; spectrally resolvable inorganic fluorescent semiconductors nanocrystals (i.e., quantum dots); microparticles; metal nanoparticles (e.g., gold, silver, copper, platinum, etc.); nanoclusters; paramagnetic metal ions; enzymes; colorimetric labels (such as, for example, dyes, colloidal gold, and the like); biotin; dioxigenin; haptens; and proteins for which antisera or monoclonal antibodies are available.

In some embodiments, the detectable moiety is biotin. Biotin can be bound to avidins (such as streptavidin), which are typically conjugated (directly or indirectly) to other moieties (e.g., fluorescent moieties) that are detectable themselves.

Below are described some non-limiting examples of other detectable moieties.

Fluorescent Dyes

In certain embodiments, a detectable moiety is a fluorescent dye. Numerous known fluorescent dyes of a wide variety of chemical structures and physical characteristics are suitable for use in the practice of the present invention. A fluorescent detectable moiety can be stimulated by a laser with the emitted light captured by a detector. The detector can be a charge-coupled device (CCD) or a confocal microscope, which records its intensity.

Suitable fluorescent dyes include, but are not limited to, fluorescein and fluorescein dyes (e.g., fluorescein isothiocyanine or FITC, naphthofluorescein, 4',5'-dichloro-2',7'-dimethoxyfluorescein, 6-carboxyfluorescein or FAM, etc.), carbocyanine, merocyanine, styryl dyes, oxonol dyes, phycoerythrin, erythrosin, eosin, rhodamine dyes (e.g., carboxytetramethyl-rhodamine or TAMRA, carboxyrhodamine 6G, carboxy-X-rhodamine (ROX), lissamine rhodamine B, rhodamine 6G, rhodamine Green, rhodamine Red, tetramethylrhodamine (TMR), etc.), coumarin and coumarin dyes (e.g., methoxycoumarin, dialkylaminocoumarin, hydroxycoumarin, aminomethylcoumarin (AMCA), etc.), Oregon Green Dyes (e.g., Oregon Green 488, Oregon Green 500, Oregon Green 514, etc.), Texas Red, Texas Red-X, SPECTRUM RED™, SPECTRUM GREEN™, cyanine dyes (e.g., CY-3™, CY-5™, CY-3.5™, CY-5.5™, etc.), ALEXA FLUOR™ dyes (e.g., ALEXA FLUOR™ 350, ALEXA FLUOR™ 488, ALEXA FLUOR™ 532, ALEXA FLUOR™ 546, ALEXA FLUOR™ 568, ALEXA FLUOR™ 594, ALEXA FLUOR™ 633, ALEXA FLUOR™ 660, ALEXA FLUOR™ 680, etc.), BODIPY™ dyes (e.g., BODIPY™ FL, BODIPY™ R6G, BODIPY™ TMR, BODIPY™ TR, BODIPY™ 530/550, BODIPY™ 558/568, BODIPY™ 564/570, BODIPY™ 576/589, BODIPY™ 581/591, BODIPY™ 630/650, BODIPY™ 650/665, etc.), IRDyes (e.g., IRD40, IRD 700, IRD 800, etc.), and the like. For more examples of suitable fluorescent dyes and methods for coupling fluorescent dyes to other chemical entities such as proteins and peptides, see, for example, "The Handbook of Fluorescent Probes and Research Products", 9th Ed., Molecular Probes, Inc., Eugene, Oreg. Favorable properties of fluorescent labeling agents include high molar absorption coefficient, high fluorescence quantum yield, and photostability. In some embodiments, labeling fluorophores exhibit absorption and emission wavelengths in the visible (i.e., between 400 and 750 nm) rather than in the ultraviolet range of the spectrum (i.e., lower than 400 nm).

A detectable moiety may include more than one chemical entity such as in fluorescent resonance energy transfer (FRET). Resonance transfer results an overall enhancement of the emission intensity. For instance, see Ju et. al. (1995) Proc. Nat'l Acad. Sci. (USA) 92: 4347, the entire contents of which are herein incorporated by reference. To achieve resonance energy transfer, the first fluorescent molecule (the "donor" fluor) absorbs light and transfers it through the resonance of excited electrons to the second fluorescent molecule (the "acceptor" fluor). In one approach, both the donor and acceptor dyes can be linked together and attached to the oligo primer. Methods to link donor and acceptor dyes to a nucleic acid have been described previously, for example, in U.S. Pat. No. 5,945,526 to Lee et al., the entire contents of which are herein incorporated by reference. Donor/acceptor pairs of dyes that can be used include, for example, fluorescein/tetramethylrohdamine, IAEDANS/fluorescein, EDANS/DABCYL, fluorescein/fluorescein, BODIPY FL/BODIPY FL, and Fluorescein/QSY 7 dye. See, e.g., U.S. Pat. No. 5,945,526 to Lee et al. Many of these dyes also are commercially available, for instance, from Molecular Probes Inc. (Eugene, Oreg.). Suitable donor fluorophores include 6-carboxyfluorescein (FAM), tetrachloro-6-carboxyfluorescein (TET), 2'-chloro-7'-phenyl-1,4-dichloro-6-carboxyfluorescein (VIC), and the like.

Enzymes

In certain embodiments, a detectable moiety is an enzyme. Examples of suitable enzymes include, but are not limited to, those used in an ELISA, e.g., horseradish peroxidase, beta-galactosidase, luciferase, alkaline phosphatase, etc. Other examples include beta-glucuronidase, beta-D-glucosidase, urease, glucose oxidase, etc. An enzyme may be conjugated to a molecule using a linker group such as a carbodiimide, a diisocyanate, a glutaraldehyde, and the like.

Radioactive Isotopes

In certain embodiments, a detectable moiety is a radioactive isotope. For example, a molecule may be isotopically-labeled (i.e., may contain one or more atoms that have been replaced by an atom having an atomic mass or mass number different from the atomic mass or mass number usually found in nature) or an isotope may be attached to the molecule. Non-limiting examples of isotopes that can be incorporated into molecules include isotopes of hydrogen, carbon, fluorine, phosphorous, copper, gallium, yttrium, technetium, indium, iodine, rhenium, thallium, bismuth, astatine, samarium, and lutetium (i.e., 3H, 13C, 14C, 18F, 19F, 32P, 35S, 64Cu, 67Cu, 67Ga, 90Y, 99mTc, 111In, 125I, 123I, 129I, 131I, 135I, 186Re, 187Re, 201Tl, 212Bi, 213Bi, 211At, 153Sm, 177Lu).

In some embodiments, signal amplification is achieved using labeled dendrimers as the detectable moiety (see, e.g., Physiol. Genomics 3:93-99, 2000), the entire contents of which are herein incorporated by reference in their entirety. Fluorescently labeled dendrimers are available from Genisphere (Montvale, N.J.). These may be chemically conjugated to the oligonucleotide primers by methods known in the art.

In Situ Hybridization

As used herein, the term "hybridized in situ" or "in situ hybridization" refers to a method in which probes hybridize to amplified nucleic acids of interest (e.g., target or reference nucleic acids) in the place where the amplified nucleic acid products are formed. For example, if bridge PCR is used to amplify nucleic acids, in situ hybridization refers to a method in which the probes specific to target nucleic acids and/or reference nucleic acids are hybridized to the PCR amplified nucleic acid colonies in the place where the colonies were (are) formed.

In some embodiments, the nucleic acid colonies according to the invention can be prepared for hybridization as described herein. Such preparation involves the treatment of the colonies so that all or part of the nucleic acid templates making up the colonies is present in a single stranded form. This can be achieved for example by heat denaturation of any double stranded DNA in the colonies. Alternatively the colonies may be treated with a restriction endonuclease specific for a double stranded form of a sequence in the template nucleic acid. For example, the endonuclease may be specific for either a sequence contained in the adaptor sequences A3' or A5'. After digestion the colonies are heated so that double stranded DNA molecules are separated and the colonies are washed to remove the non-immobilized strands thus leaving attached single stranded DNA in the colonies.

After preparation of the colonies for hybridization, appropriate probes are added to the colonies under conditions appropriate for the hybridization of the probes with its specific target sequences. Such conditions may be determined by a person skilled in the art using known methods and will depend on for example the sequence of the probe.

In some embodiments, hybridization can be performed using multiple probes at the same time. For example, probes specific to both the target and reference nucleic acids can be hybridized in one reaction. In some embodiments, hybridization can be carried out in different rounds. For example, probes specific for one region can be hybridized and detected first then removed by heat denaturation and, probes specific for a second region may be hybridized and detected. These steps may be repeated as many times as is desired.

Labeled probes which are hybridized to nucleic acid colonies can then be detected using apparatus including an appropriate detection device. In some embodiments, detection system for fluorescent labels is a charge-coupled device (CCD) camera, which can optionally be coupled to a magnifying device, for example a microscope. Using such technology it is possible to simultaneously monitor many colonies in parallel. For example, a CCD camera can be used with a microscope with a 10× or 20× objective. In some embodiments, colonies over a surface of between 1 mm$^2$ and 4 mm$^2$ can be observed at same time. In some embodiments, between 10,000 and 1,000,000 colonies are observed in parallel. In some embodiments, between 10,000 and 500,000 colonies are observed in parallel. In some embodiments, between 10,000 and 200,000 colonies are observed in parallel. Or, ranges within these ranges may be used. Moreover, it is anticipated that this number will increase with improved optics and larger chips.

Alternatively or additionally, methods of monitoring the colonies generated include scanning the surface covered with colonies. For example, CCD camera can be used to take pictures of a surface covered with any number of colonies.

Any other devices allowing detection and preferably quantitation of fluorescence on a surface may be used to monitor the nucleic acid colonies of the invention. For example fluorescent imagers or confocal microscopes could be used.

In some embodiments, if bead emulsion PCR is used for single molecule amplification, in situ hybridization can be carried out by mixing the beads containing amplified nucleic acid colonies with appropriate probes. In some embodiments, flow cytometry can be used to detect the labeled beads. For example, the bead suspension can be diluted to a concentration of—106-107 beads per ml in 10 mMTris-HCl, 1 mMEDTA (351-010-131, Quality Biological, Inc., Gaithersburg, Md.) and analyzed using a LSR instrument (BD Biosciences, Franklin Lakes, N.J.). The instrument may be set up for standard two-color analysis using an argon laser and optical filters that distinguished between the two fluorescent dyes. In some embodiments, no spectral deconvolution is required as the major bead populations are well separated. In some cases, scanning is performed with FACScan or FACSCalibur instruments (BD Biosciences).

Array-Based Hybridization

In some embodiments, nucleic acid colonies containing amplified products can be detected using array-based hybridization methods. In general, probe arrays including probes specific to target and/or reference nucleic acids can be used to hybridize amplified nucleic acids. Array-based hybridization may be performed using microchips, multi-well plates, micro-machined glass slides, microfluidic devices, and various other means known in the art.

In some embodiments, amplified nucleic acids can be harvested, pooled and hybridized against probe arrays including probes specific to target and/or reference nucleic acids. Colonies containing amplified nucleic acids can be removed from the support by, for example, restriction enzyme digestion specific a sequence in the capturing oligonucleotides, a sequence contained in the adaptor sequences A3' or A5', or other sequences in the template. The harvested DNA can be heated such that double stranded DNA molecules are separated.

In some embodiments, DNA harvested as described above is diluted so that there is, on average, one polynucleotide from amplified products per detection site (e.g., per well).

Thus, when the individual discrete template is analyzed for the presence of the nucleic acid of interest (e.g., target or reference nucleic acid), each detection site will, on average, either be present or absent of target or reference nucleic acid. Therefore, typically, each reaction site has one of the following results: no signal, labeled with signal associated with target nucleic acid or labeled with signal associated with the reference nucleic acid.

Thus, in some embodiments, array-hybridization is based on single molecule analysis on each detection site, and the amount of target of interest (e.g., chromosome 21 trisomy) can be determined based on the results of a large number of detection sites.

In some embodiments, a probe suitable for array-based hybridization is a quenched fluorescent probe. The quenched fluorescent probe typically comprises an oligonucleotide designed to hybridize to a nucleic acid, typically a PCR amplification product of interest (e.g., an amplicon from a target locus or reference locus) conjugated to a fluorophore and to a fluorescent quencher. The fluorescent quencher is normally in proximity to the fluorophore on a given probe; therefore, no signal can be detected from the fluorophore. When a probe molecule is hybridized to a nucleic acid template, the fluorophore can be released from the probe. Once released from the probe and (thus away from the quencher), a fluorophore can be detected. When excited by the appropriate wavelength, the fluorophore will emit light of a particular wavelength spectrum characteristic of that fluorophore. Typically, detectable signal from the fluorophore can be attributable to target or reference nucleic acids (e.g., difference chromosomes).

Any of a variety of fluorophores may be used, as are methods for conjugating them to probes. (See, for example, R. P. Haugland, "*Molecular Probes: Handbook of Fluorescent Probes and Research Chemicals* 1992-1994", 5th Ed., 1994, Molecular Probes, Inc.). Non-limiting examples of suitable fluorophores include fluorescein, rhodamine, phycobiliproteins, cyanine, coumarin, pyrene, green fluorescent protein, BODIPY®, and their derivatives. Both naturally occurring and synthetic derivatives of fluorophores can be used. Examples of fluorescein derivatives include fluorescein isothiocyanate (FITC), Oregon Green, Tokyo Green, seminapthofluorescein (SNAFL), and carboxynaphthofluorescein. Examples of rhodamine derivatives include rhodamine B, rhodamine 6G, rhodamine 123, tetramethyl rhodamine derivatives TRITC and TAMRA, sulforhodamine 101 (and its sulfonyl chloride form Texas Red), and Rhodamine Red. Phycobiliproteins include phycoerythrin, phycocyanin, allophycocyanin, phycoerythrocyanin, and peridinin chlorophyll protein (PerCP). Types of phycoerythrins include R-phycoerythrin, B-phycoerythrin, and Y-phycoerythrin. Examples of cyanine dyes and their derivatives include Cy2 (cyanine), Cy3 (indocarbocyanine), Cy3.5, Cy5 (indodicarbocyanine), Cy5.5, Cy7, BCy7, and DBCy7. Examples of green fluorescent protein derivatives include enhanced green fluorescent protein (EGFP), blue fluorescent protein (BFP), cyan fluorescent protein (CFP), and yellow fluorescent protein (YFP). BODIPY® dyes (Invitrogen) are named either for the common fluorophore for which they can substitute or for their absorption/emission wavelengths. BODIPY® dyes include BODIPY FL, BODIPY R6G, BODIPY TMR, BODIPY TR, BODIPY 581/591, BODIPY 630/650, and BODIPY 650/665.

Detection Methods

Various methods can be used to detect target nucleic acids and to determine relative amount of the target nucleic acids. In certain embodiments, amounts of a target nucleic acid relative to that of a reference nucleic acid are determined based on a comparison of signals, and/or of numerical values representative of such signals, indicative a target nucleic acid or a reference nucleic acid. Signals "indicative of a target nucleic acid are typically associated with a reaction site or detection site for the target nucleic acid; similarly, signals "indicative of" a reference nucleic acid are typically associated with a reaction site or detection site for the reference nucleic acid.

In some embodiments, signals emanate from one or more detectably labeled probes that become associated with the relevant reaction site or detection site. In some embodiments, a detectably labeled probe is a nucleic acid probe that can hybridize to and is specific for a target nucleic acid or to a reference nucleic acid. In some embodiments, signals emanate from an entity (e.g., a detectable moiety) that is physically associated with a probe at the time the signal is detected. In some embodiments, signals emanate from an entity that is not physically associated with a probe at the time the signal is detected. For example, signals may emanate from an entity that is released from a probe upon hybridization of the probe to its nucleic acid complement (e.g., target nucleic acid or portion thereof or reference nucleic acid or portion thereof).

Signals indicative of target nucleic acids are generally distinguishable from signals indicative of reference nucleic acid. For example, in some embodiments, probes specific for a target nucleic acid (or a portion thereof) and probes specific for the reference nucleic acid (or a portion thereof) are labeled with distinctively detectable signals. In some embodiments, these distinctively detectable signals are distinct optical signals, such as, for example, distinct fluorescent or luminescent signals. For example, in embodiments in which probes are labeled with fluorescent moieties, probes specific for the target nucleic acid (or a portion thereof) may be labeled with fluorescent moieties that have a different emission spectrum (i.e., color and wavelength) than that of the fluorescent moieties with which the probes specific for the reference nucleic acid (or a portion thereof) are labeled. For example, fluorophores that emit green can be used to label probes specific to the target nucleic acid (e.g., chromosome 21) and fluorophores that emit red can be used to label probes specific to the reference nucleic acid (e.g., chromosome 1), or vice versa.

In certain embodiments, the amount or copy number of the target nucleic acid relative to a reference nucleic acid is determined. In some embodiments, relative amount or copy number is expressed as the ratio of the amount or copy number of a target nucleic acid (per genome) to the copy number of a single copy reference nucleic acid in a nucleic acid sample. In some embodiments, this ratio is expected to be 1.

In some embodiments, determining the relative copy number of the target nucleic acid comprises steps of (a) determining a first fluorescent signal level indicative of a first number of detection sites containing the target nucleic acid, or a portion thereof; (b) determining a second fluorescent signal level indicative of a second number of detection sites containing the reference nucleic acid, or a portion thereof; (c) determining a ratio of the first fluorescent signal level to the second fluorescent signal level; and (d) determining the relative copy number of the target nucleic acid by normalizing the ratio determined in step (c) to the ratio between the number of probes specific for the target nucleic acid and the number of probes specific for the reference nucleic acid. Typically, fluorescent signal levels are normalized to background signal levels.

Means for carrying out hybridization of probes to target nucleic acids (or a portion thereof) or reference nucleic acids (or a portion thereof) may be in communication with one or more devices or machines to facilitate detection. For example, a means for carrying out hybridization may be in communication with one or more microscopes, diodes, light stimulating devices (e.g., lasers), photomultiplier tubes, processors, or combinations thereof. Such devices may be used to detect a signal associated with a target nucleic acid or reference nucleic acid. Typically the signal is an optical signal and an optical detector is used. Optical detectors can include one or more of photodiodes (e.g., avalanche photodiodes), a fiber-optic light guide leading, for example, to a photomultiplier tube, a microscope, and/or a video camera (e.g., a charged couple device (CCD) camera).

Detectors can be fabricated as part of, or physically attached to, the platform or means for carrying out hybridization. Alternatively or additionally, a scanning system is used. For example, certain automated systems can scan a light source relative to the means for hybridization, and certain automated systems can scan the emitted light over a detector, or include a multichannel detector. By way of an illustrative example, a means for hybridization can be attached to a translatable stage and scanned under a microscope objective. A signal so acquired is then routed to a processor for signal interpretation and processing. In some embodiments, arrays of photomultiplier tubes are used. In some embodiments, optical systems that have the capability of collecting signals from different reaction sites or detection sites simultaneously while determining the signal from each reaction site or detection site are used.

In some embodiments, a detector uses a CCD camera and an optical path that provides for a large field of view and a high numerical aperture to maximize the amount of light collected from each detection site or reaction site (or spot in the array, if an array is used). In such embodiments, the CCD is used as an array of photodetectors wherein each pixel or group of pixels corresponds to a reaction chamber rather than being used to produce an image of the array. Thus, the optics may be altered such that image quality is reduced or defocused to increased the depth of field of the optical system to collect more light from each detection site or reaction site (or spot in the array, if an array is used).

In some embodiments, a detector may include a light source for stimulating an entity ("a reporter") that generates a detectable signal. The type of light source used may depend in part on the nature of the reporter that is activated to generate the signal. Suitable light sources may include, but are not limited to, lasers, laser diodes, and high intensity lamps. In embodiments in which a laser is used, the laser can be used to scan across a set of detection sites or reaction sites, or a single detection site or reaction site, or spot(s) on an array, if an array is used. Laser diodes can be fabricated as part of the system for determining relative amounts as described herein, or can be fabricated into another device that is placed adjacent to the means for carrying out hybridization.

A number of commercially-available external detectors, including fluorescence detectors, can be used. Examples of fluorescence detectors that may be used in accordance with the invention include, but are not limited to, Applied Precision Array WoRx (Applied Precision, Issaquah, Wash.). In embodiments using microarrays, machines such as the GENEPIX™ 4000B microarray reader (Axon Instruments, USA) can be used to scan fluorescent signals.

Typically, detectable labels are selected so that their respective optical signals can be related to the quantity of labeled nucleic acids present and so that the optical signals generated by different light-generating labels can be compared. Measurement of the emission intensities of fluorescent labels is a typical means of meeting this design objective. For a given selection of fluorescent dyes, relating their emission intensities to the respective quantities of labeled nucleic acids involves consideration of several factors, including fluorescent emission maxima of the different dyes, quantum yields, emission bandwidths, absorption maxima, absorption bandwidths, nature of excitation light source(s), and the like. Guidance for making fluorescent intensity measurements and for relating them to quantities of analytes is available in the literature relating to chemical and molecular analysis, e.g. Guilbault, editor, Practical Fluorescence, Second Edition (Marcel Dekker, New York, 1990); Pesce et al., editors, Fluorescence Spectroscopy (Marcel Dekker, New York, 1971); White et al., Fluorescence Analysis: A Practical Approach (Marcel Dekker, New York, 1970); and the like.

As used herein, the term "relative optical signal" means a ratio of signals from different light-generating labels that can be related to a ratio of differently labeled nucleic acids. In some embodiments, a relative optical signal is a ratio of fluorescence intensities of two or more different fluorescent dyes.

In certain embodiments, signals are converted to numerical values using standard software known in the art. In some embodiments, signals (or numerical values representative of signals) are normalized based on background signals.

In some embodiments, signals (or numerical values representative of signals) are normalized based on the number of probes used that are specific for the target nucleic acid (or a portion thereof) relative to the number of probes used that are specific for the reference nucleic acid (or a portion thereof). For example, the number of probes used that are specific for the target nucleic acid (or a portion thereof) may be different than the number of probes used that are specific for the reference nucleic acid (or a portion thereof); thus, normalization of the signals based on the number of probes used allows an accurate comparison of the relative amount of target nucleic acid. In some embodiments, the signals (or numerical values representative of signals) are normalized based on the number of the detectable moieties present in all of the probes used that are specific for the target nucleic acid (or a portion thereof) relative to the number of detectable moieties present in all of the probes used that are specific for the reference nucleic acid (or a portion thereof). In some embodiments, different probes may have different numbers of detectable moieties. For example, for nucleic acid probes that are labeled with a labeled deoxynucleotide, the number of detectable moieties in each probe may depend on the sequence of the probe and/or length of the probe). In such embodiments, normalization based on the total number of detectable moieties present in all of the probes specific for a target nucleic acid (or a portion thereof) as compared to the total number of detectable moieties present in all of the probes specific for a reference nucleic acid (or a portion thereof) allows an accurate comparison of the relative amount of the target nucleic acid. In various embodiments, depending on the specifics of the probe scheme (including, for example, total number of probes used, number of detectable moieties per probe, molar amounts of each probe used, etc.) normalizations of signal (or of numerical representations of signals) are used as appropriate.

Any of a variety of software programs known in the art may be used to analyze signals as described herein, including, but not limited to, GENEPLX PRO™ 4.0.1.12 software (Axon Instruments, USA), Feature Extraction (Agilent), Matlab (Mathworks), and the like.

EXAMPLES

Example 1. Single Molecule Amplification by PCR

DNA was prepared from a biological specimen containing blood from a pregnant woman. DNA was then sheared by sonication to generate short fragments (because fetal DNA in plasma is already short, this shearing step may be optional). Adapters were ligated to each end of all sheared DNA fragments. DNA ligated with adapters was diluted into a polyacrylamide solution. The DNA/polyacrylamide solution was spread across the surface of a glass slide following standard preparation techniques to form polymerase colonies (polony PCR). The appropriate dilution of DNA may be determined empirically, such that DNA molecules can be individually resolved when spread across the slide to yield thousands to millions of spatially distinct polonies. Once the polyacrylamide was set, a solution of PCR amplification reagents with primers specific to the ligated adapter sequence were infused into the slide. Next, the slide underwent PCR thermal cycling using standard conditions to amplify DNA fragments resulting in colonies of DNA containing the regions of interest.

Example 2. Single Molecule Amplification by Rolling Circle Amplification

DNA sample was prepared and ligated with adapters as described in Example 1. Following ligation of adapters, the fragments were circularized by ligation. The circularized DNA was diluted into a polyacrylamide solution and spread across the surface of a glass slide as described in Example 1. DNA was diluted appropriately such that circularized DNA molecules can be individually resolved when spread across the slide to form thousands to millions of spatially distinct polonies. Once the polyacrylamide was set, a solution containing rolling circle amplification (RCA) reagents (including random hexamers and Phi29 or similar polymerase) was infused into the gel. Amplification proceeded using standard RCA conditions (approximately 30° C. for an extended period, typically overnight or 12 hours).

Example 3. Single Molecule Amplification by Bridge PCR

DNA sample was prepared and ligated with adapters as described in Example 1. Following ligation of adapters, DNA was diluted into a hybridization solution and spread across the surface of a glass slide coated with universal capture probes complimentary to the ligated adapters such that DNA molecules with adapters can be hybridized to the capture probes on the surface of the slide. A solution containing nucleotides and polymerase enzyme was added to the slide and bridge amplification was performed to generate clonal populations of the fragments.

Example 4. Hybridization and Target Detection

For samples amplified in polyacrylamide gel on a slide, a solution of fluorescently labeled oligonucleotide probes specific for a target chromosome and a reference chromosome was infused into the slide. The target may be a locus or combinations of loci on chromosome 21, 18 or 13 (or any other disease relevant chromosome) and the reference may be a locus or combinations of loci on chromosome 1, 2, 6, 11, or any other chromosome that is distinct from the target. The fluorescent label for the target probes was a different color than the label used for the reference probes. For example, the target probes were labeled with CY3 dye (green), while the reference probes were labeled using CY5 (red). The slide was then subjected to conditions that allow probes to hybridize specifically to their complimentary DNA targets. Next, unhybridized probes were washed out of the slide through a series of washes.

Alternatively, for samples amplified by bridge PCR, a solution of fluorescently labeled oligonucleotide probes specific for the target and reference chromosomes was spread across the slide and allowed to hybridize to their complimentary DNA fragments. Following hybridization, unhybridized probes were washed off the slide.

Finally, slides were imaged in a commercial laser scanner. The number of target and reference chromosome hybridization events were counted; i.e., count how many green and red dots are present on the slide. The ratio of these events was calculated to determine if a copy number aberration exists in the specimen.

EQUIVALENTS AND SCOPE

Those skilled in the art will recognize, or be able to ascertain using no more than routine experimentation, many equivalents to the specific embodiments, described herein. The scope of the present invention is not intended to be limited to the above Description, but rather is as set forth in the appended claims.

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any cell type; any neuronal cell system; any reporter of synaptic vesicle cycling; any electrical stimulation system; any imaging system; any synaptic vesicle cycling assay; any synaptic vesicle cycle modulator; any method of use; etc.) can be excluded from any one or more claims, for any reason, whether or not related to the existence of prior art.

INCORPORATION OF REFERENCES

All publications and patent documents cited in this application are incorporated by reference in their entirety to the same extent as. if the contents of each individual publication or patent document were incorporated herein.

What is claimed is:

1. A method of determining the relative amount of a target nucleic acid in a biological sample, the method comprising:
   amplifying polynucleotides immobilized at the individual sites to generate amplified products,
   wherein the polynucleotides are obtained from a biological sample,
   wherein the polynucleotides comprise heterogeneous nucleic acids comprising a target nucleic acid and a reference nucleic acid, and
   wherein the each individual site contains on average one of the polynucleotides;
   hybridizing the amplified products with nucleic acid probes specific for (i) a target nucleic acid, or a portion thereof, and (ii) a reference nucleic acid, or a portion thereof, at respective individual sites on the solid support;
   determining (i) a first number of individual sites containing probes hybridized to a target nucleic acid, or a portion thereof, and (ii) a second number of individual sites containing probes hybridized to a reference nucleic acid, or a portion thereof; and
   comparing the first number to the second number to determine the relative amount of the target nucleic acid in the biological sample.

2. The method claim 1, wherein the nucleic acid probes specific for the target nucleic acid, or a portion thereof, are specific for a single locus.

3. The method of claim 1, wherein the nucleic acid probes specific for the target nucleic acid, or a portion thereof, are specific for multiple loci.

4. The method of claim 1, wherein the nucleic acid probes specific for the target nucleic acid, or a portion thereof, are multiplexed.

5. The method of claim 4, wherein the multiplexed probes comprise 2-10,000 probes.

6. The method of claim 5, wherein the multiplexed probes specific for the target nucleic acid, or a portion thereof, comprise 500 probes.

7. The method of claim 1, wherein the nucleic acid probes specific for the reference nucleic acid, or a portion thereof, are specific for a single locus.

8. The method of claim 1, wherein the nucleic acid probes specific for the target nucleic acid, or a portion thereof, are specific for multiple loci.

9. The method of claim 1, wherein the nucleic acid probes specific for the reference nucleic acid, or a portion thereof, are multiplexed.

10. The method of claim 9, wherein the multiplexed probes comprise 2-10,000 probes.

11. The method of claim 9, wherein the multiplexed probes specific for the reference nucleic acid, or a portion thereof, comprise 500 probes.

12. The method claim 1, wherein the probes specific for the target nucleic acid, or a portion thereof, and the probes specific for the reference nucleic acid, or a portion thereof, are labeled with distinctively detectable signals.

13. The method of claim 12, wherein the distinctively detectable signals are different optical signals.

14. The method of claim 13, wherein the different optical signals are distinct fluorescent or luminescent signals.

15. A method for detecting a target nucleic acid in a biological sample, comprising:
   amplifying the polynucleotides immobilized at individual sites on a solid support to generate a plurality of clusters such that each cluster contains amplified nucleic acid product
   wherein the polynucleotides are obtained from a biological sample and comprise heterogeneous nucleic acids comprising a target nucleic acid and a reference nucleic acid, and wherein the each individual site contains on average one polynucleotide; and
   detecting clusters or reaction sites containing the target nucleic acid, or a portion thereof, by hybridization using one or more probes specific for the target nucleic acid, thereby detecting the target nucleic acid in the biological sample.

* * * * *

SEQUENCE LISTING

```
<160> NUMBER OF SEQ ID NOS: 2

<210> SEQ ID NO 1
<211> LENGTH: 9
<212> TYPE: DNA
<213> ORGANISM: Artificial Sequence
<220> FEATURE:
<223> OTHER INFORMATION: synthetic nucleotide sequence

<400> SEQUENCE: 1 gcggtccca                                                                 9

<210> SEQ ID NO 2
<211> LENGTH: 9
<212> TYPE: DNA
<213> ORGANISM: Artificial Sequence
<220> FEATURE:
<223> OTHER INFORMATION: synthetic nucleotide sequence

<400> SEQUENCE: 2 tgggaccgc                                                                 9
```